(12) United States Patent
Mizuno et al.

(10) Patent No.: US 7,898,577 B2
(45) Date of Patent: Mar. 1, 2011

(54) LIGHT SOURCE DEVICE AND IMAGE PICKUP DEVICE

(75) Inventors: Kyosuke Mizuno, Hachioji (JP); Shinji Yamashita, Tachikawa (JP)

(73) Assignee: Olympus Medical Systems, Corp. (JP)

( * ) Notice: Subject to any disclaimer, the term of this patent is extended or adjusted under 35 U.S.C. 154(b) by 286 days.

(21) Appl. No.: 11/910,103

(22) PCT Filed: Mar. 30, 2006

(86) PCT No.: PCT/JP2006/306713
§ 371 (c)(1),
(2), (4) Date: Aug. 15, 2008

(87) PCT Pub. No.: WO2006/106853
PCT Pub. Date: Oct. 12, 2006

(65) Prior Publication Data
US 2009/0080175 A1   Mar. 26, 2009

(30) Foreign Application Priority Data
Mar. 31, 2005 (JP) ................................. 2005-101651

(51) Int. Cl.
*H04N 9/73* (2006.01)
*H04N 5/232* (2006.01)
(52) U.S. Cl. ..................................... 348/223.1; 348/354
(58) Field of Classification Search ............... 348/223.1, 348/354
See application file for complete search history.

(56) References Cited

U.S. PATENT DOCUMENTS

| | | | |
|---|---|---|---|
| 5,460,182 A | 10/1995 | Goodman et al. | |
| 5,748,236 A * | 5/1998 | Shibazaki | 348/270 |
| 6,488,390 B1 * | 12/2002 | Lebens et al. | 362/231 |
| 6,542,238 B1 * | 4/2003 | Tsuboi et al. | 356/401 |
| 7,256,833 B2 * | 8/2007 | Shaw et al. | 348/370 |
| 2002/0191102 A1 * | 12/2002 | Yuyama et al. | 348/370 |
| 2005/0046739 A1 * | 3/2005 | Voss et al. | 348/371 |
| 2008/0239910 A1 * | 10/2008 | Kikuchi et al. | 369/53.22 |

FOREIGN PATENT DOCUMENTS

| | | |
|---|---|---|
| EP | 1 318 670 A1 | 6/2003 |
| JP | 7-275200 | 10/1995 |
| JP | 11-253397 | 9/1999 |
| JP | 2000-124683 | 4/2000 |

(Continued)

OTHER PUBLICATIONS

International Search Report and Written Opinion dated May 23, 2006 issued in corresponding International Patent Appln. No. PCT/JP2006/306713.

(Continued)

*Primary Examiner* — Sinh Tran
*Assistant Examiner* — Hung H Lam
(74) *Attorney, Agent, or Firm* — Ostrolenk Faber LLP

(57) ABSTRACT

A light source device which causes a sufficiently bright subject image to be obtained is provided.

The light source device includes a first light-emitting diode 10-1 which generates illumination light to be applied to a subject, a second light-emitting diode 10-2 which generates illumination light with wavelength different from the illumination light generated from the first light-emitting diode 10-1, and a light-emitting diode drive control section 3 which independently controls integrated output values (light emission intensities, light emission periods) of the first light-emitting diode 10-1 and second light-emitting diode 10-2 in synchronism with image pickup timing at which the subject is photographed.

8 Claims, 23 Drawing Sheets

FOREIGN PATENT DOCUMENTS

| JP | 2002-112959 | 4/2002 |
|---|---|---|
| WO | WO 03/087653 A2 | 10/2003 |
| WO | WO 2004/062268 A1 | 7/2004 |
| WO | WO 2004/082472 A1 | 9/2004 |

OTHER PUBLICATIONS

Notification of Transmittal of International Preliminary Report on Patentability dated Aug. 21, 2008 issued in connection with PCT/JP2006/306713.

Letter from German associate dated Oct. 30, 2009 forwarding the Search Report dated Oct. 22, 2009 to Japanese associate, including discussion of relevancy thereof.

Search Report issued by European Patent Office in connection with corresponding application No. EP 06 73 0661.3 on Oct. 22, 2009.

Japanese Office Action mailed Nov. 16, 2010 in connection with corresponding Japanese Patent Application No. 2005-101651.

Japanese Patent Application No. 2005-101651.

Partial English translation of Japanese Office Action issued in connection with corresponding Japanese application provided as an explanation of prior art relevancy.

* cited by examiner

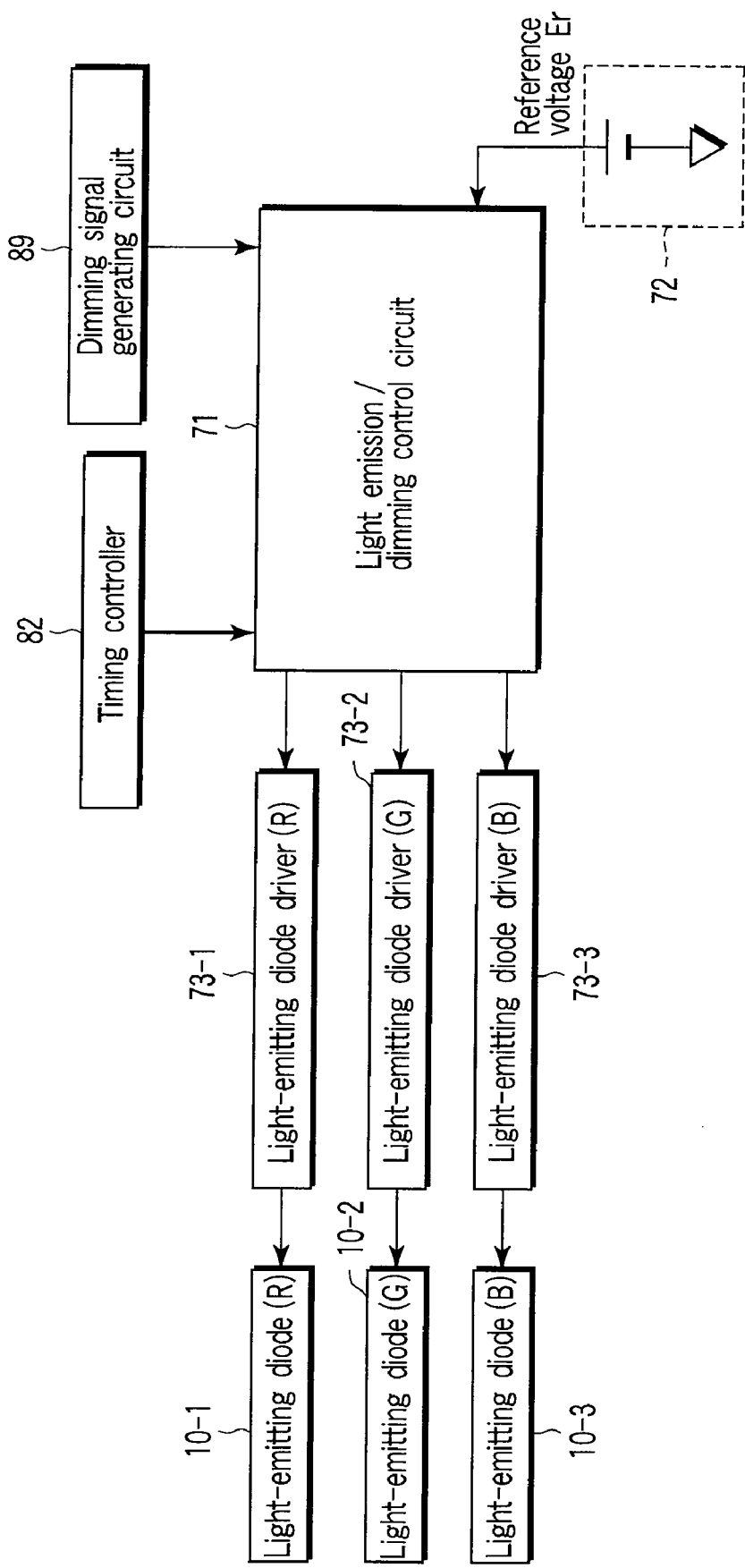
F I G. 3

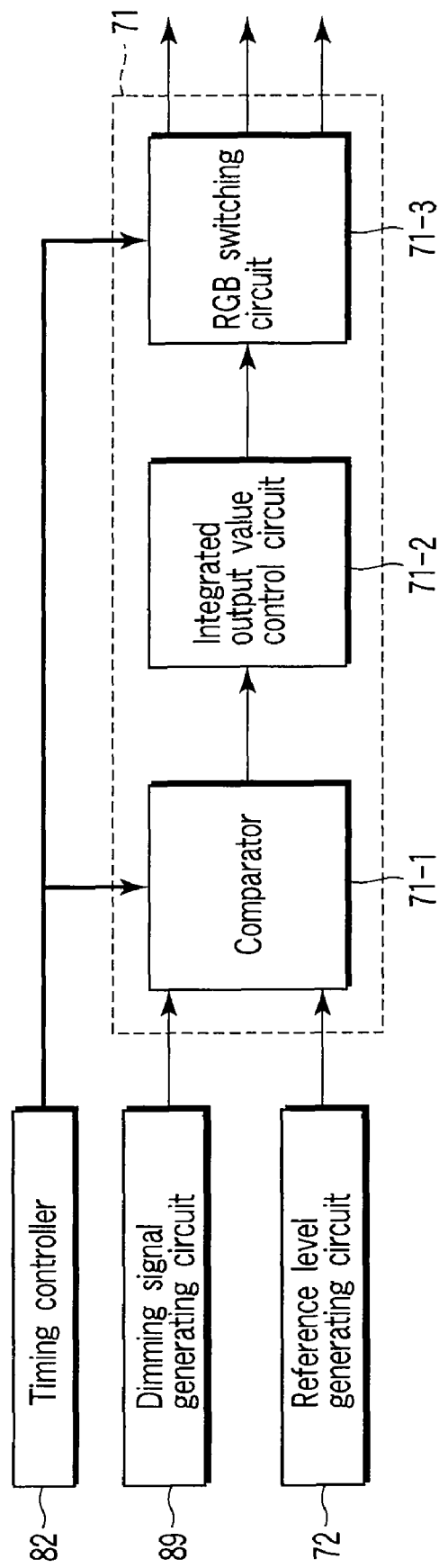
F I G. 4A

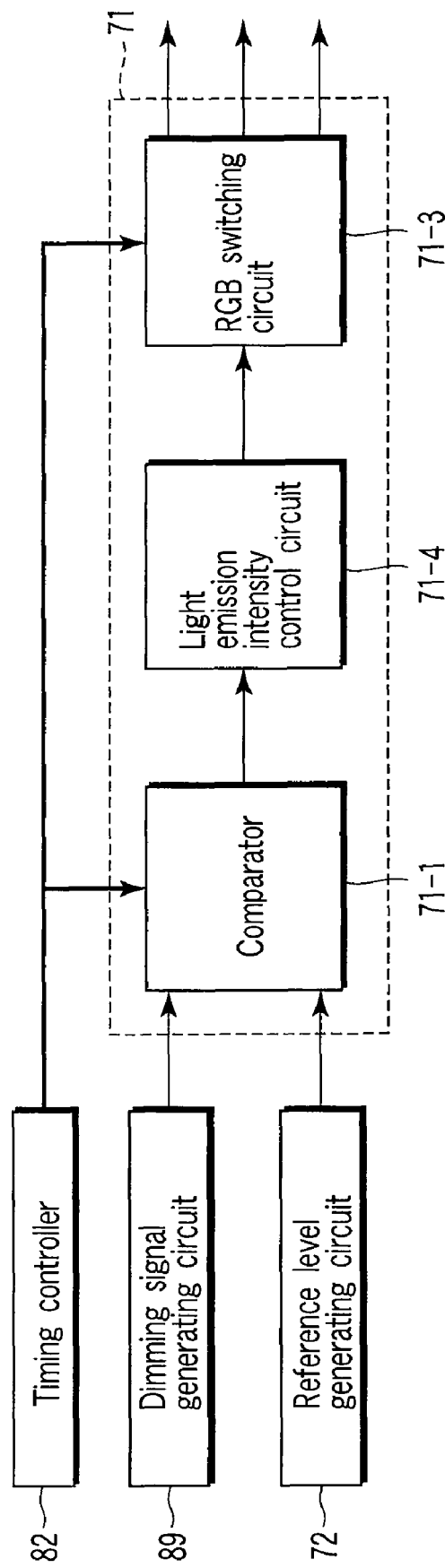
F I G. 4B

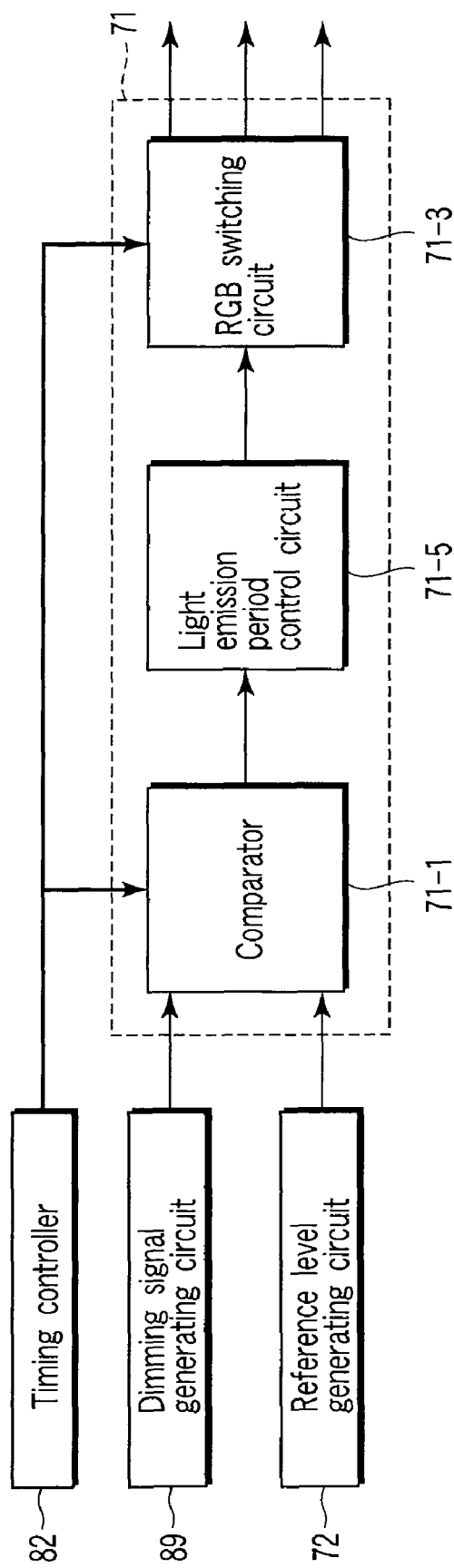
F I G. 4C

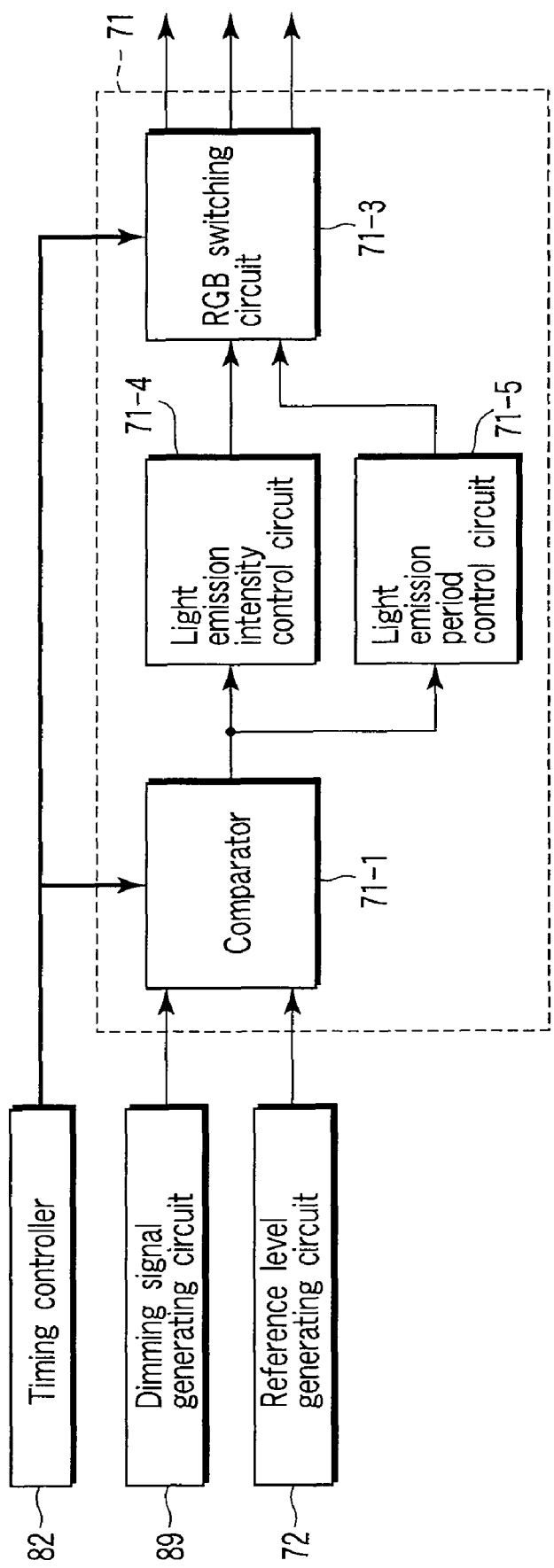
F I G. 5A

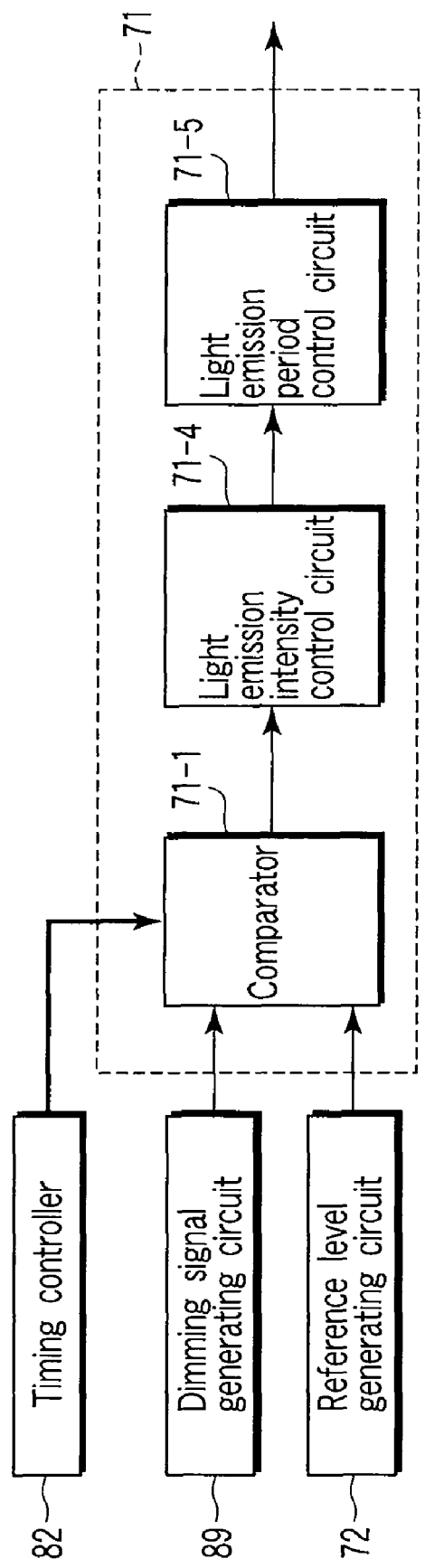
F I G. 9B

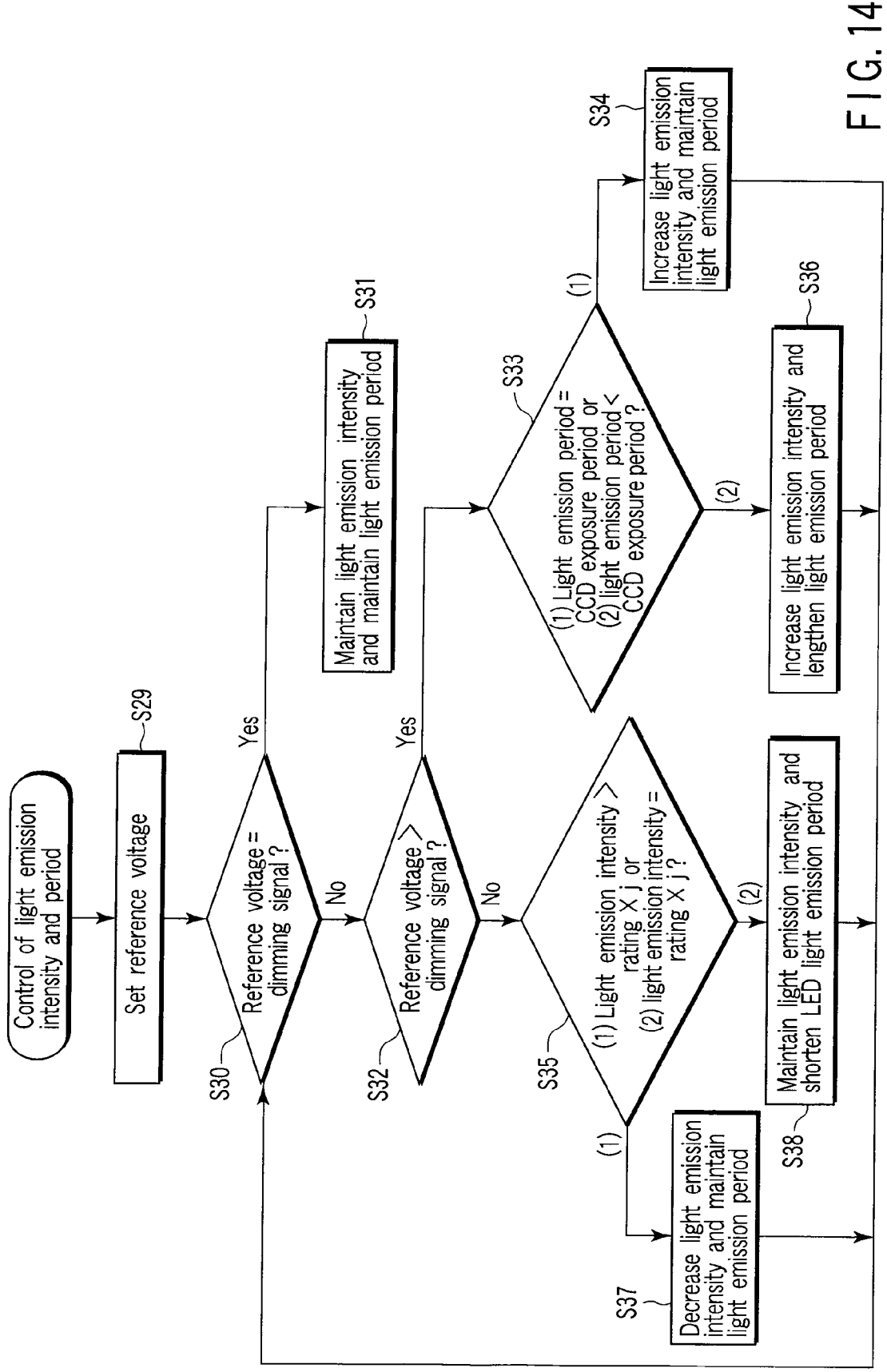
F I G. 14

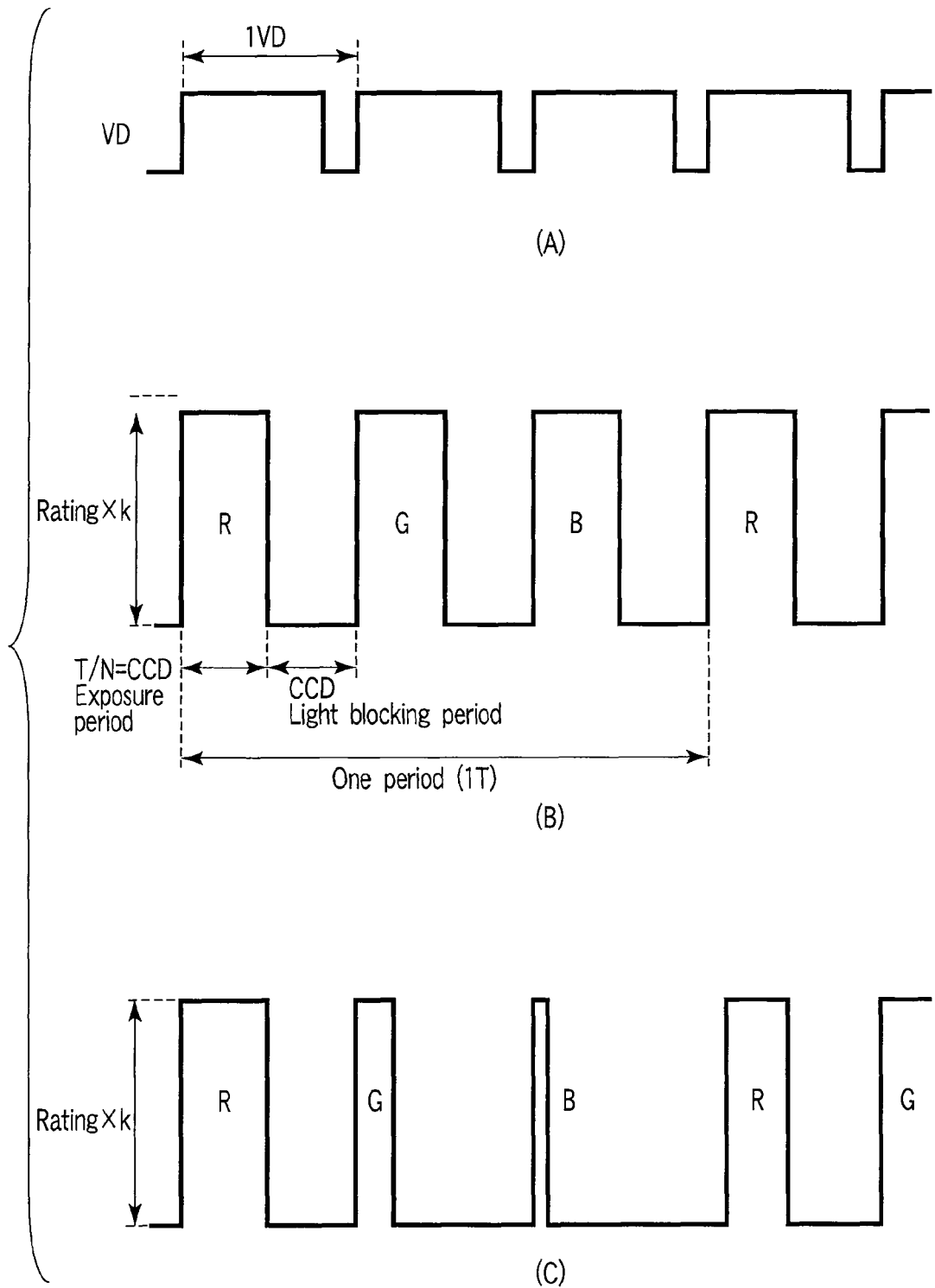
F I G. 16

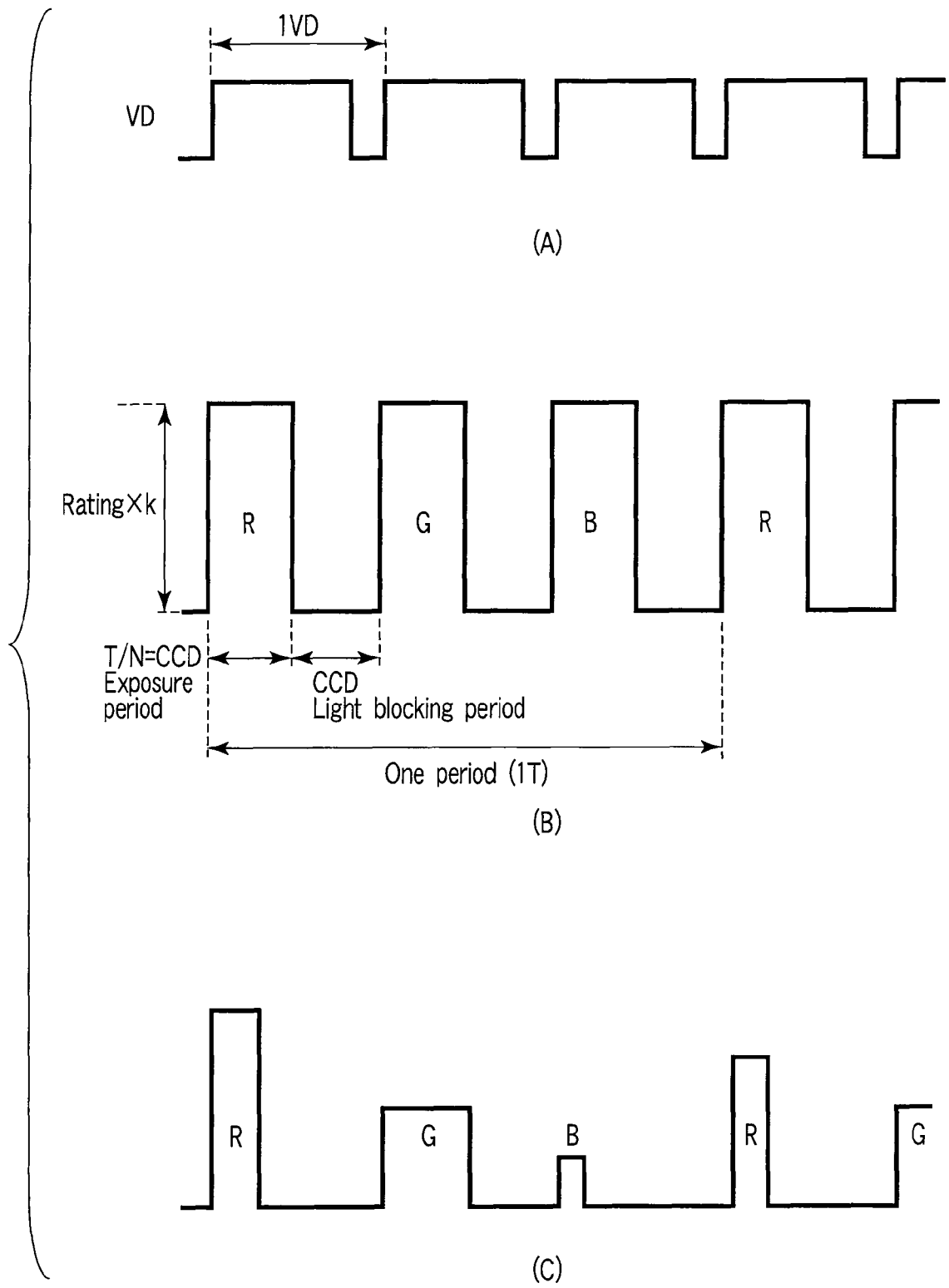
F I G. 17

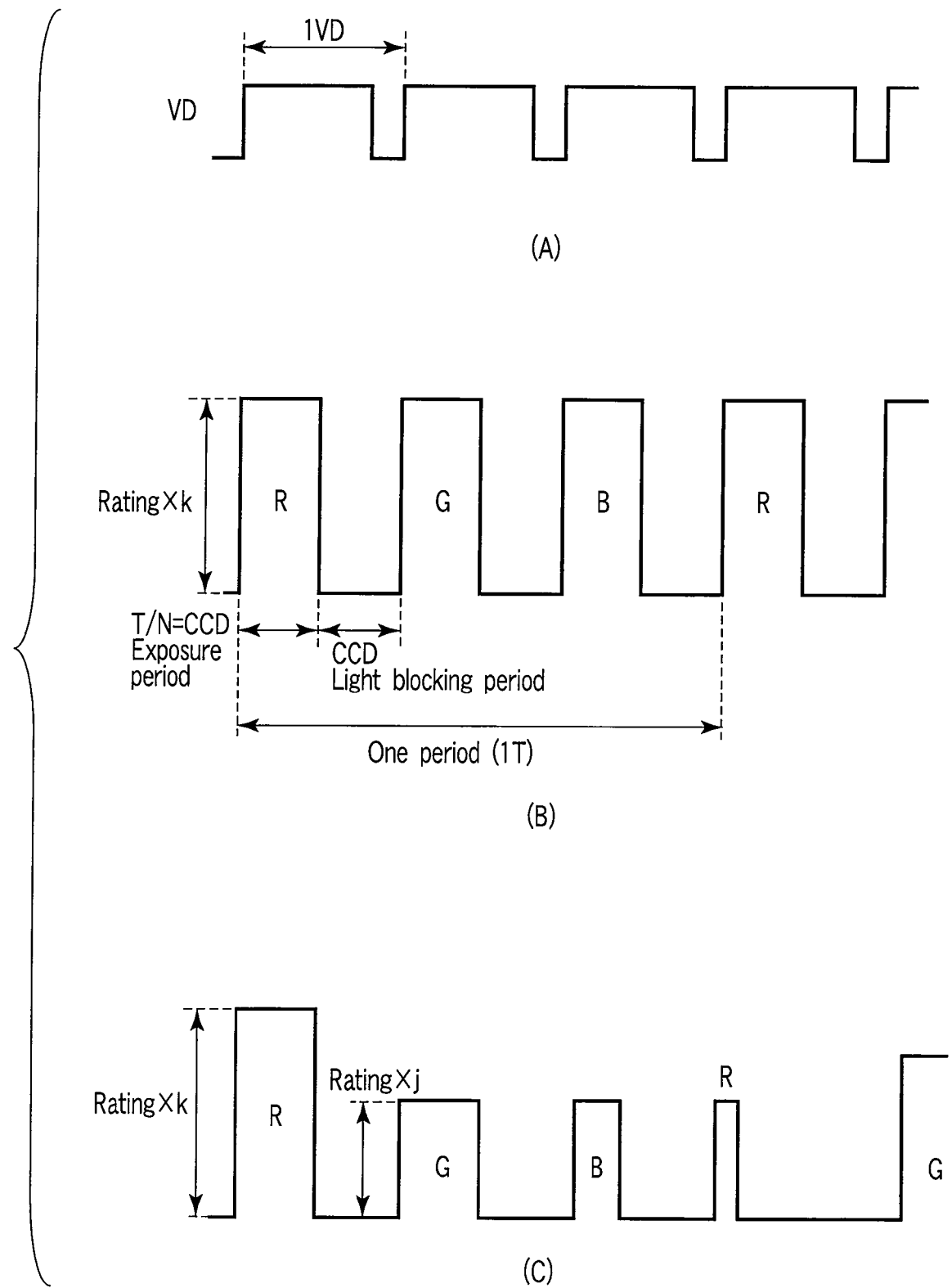
F I G. 18

LIGHT SOURCE DEVICE AND IMAGE PICKUP DEVICE

TECHNICAL FIELD

This invention relates to a light source device which selectively drives and controls a plurality of light-emitting portions and an image pickup device using the light source device.

BACKGROUND ART

For example, in an endoscope for medical use, a combination of a xenon lamp and rotating RGB color disk is conventionally known as a light source for illuminating a subject. However, there was a problem that the configuration was expensive and the configuration of the light source itself was complicated.

Therefore, there is proposed a light source device which solves the above problem by using R, G, and B light-emitting elements and sequentially pulsatively lighting the light-emitting elements in synchronism with an exposure period of the image pickup device at the rated level instead of using the xenon lamp and rotating RGB color disk as the light source device. One example of the light source device is disclosed in Jpn. Pat. Appln. KOKAI Publication No. H11-225953.

DISCLOSURE OF INVENTION

However, in the prior art represented by Jpn. Pat. Appln. KOKAI Publication No. H11-225953, there was no consideration for independently controlling the R, G, and B light-emitting elements, and therefore, it was impossible to observe the subject with the coloring most suitable for the subject.

Further, in the prior art, since the light-emitting elements were sequentially pulsatingly lit in synchronism with the timing of the exposure period of the image pickup device at the rated level, it was impossible to obtain a sufficiently bright subject image.

This invention has been made with attention paid to the above problem and an object thereof is to provide a light source device and image pickup device which permit the subject to be observed with the coloring most suitable for the subject.

Further, another object of this invention is to provide a light source device and image pickup device which permit a sufficiently bright subject image to be obtained.

To obtain the above objects, according to a first aspect of the present invention, there is provided a light source device comprising:

a first light-emitting section which generates illumination light to be applied to a subject, a second light-emitting section which generates illumination light with wavelength different from the illumination light generated from the first light-emitting section, and an integrated output value control section which independently controls integrated output values of the first light-emitting section and second light-emitting section in synchronism with image pickup timing at which the subject is photographed.

According to a second aspect of the present invention, there is provided a light source device according to the first aspect, wherein the integrated output value control section includes a comparator which compares a dimming signal generated based on an image pickup signal from an image pickup element which photographs the subject with a reference level, an integrated output value control circuit which controls the integrated output values of the first and second light-emitting sections based on the comparison result, and a light-emitting section selecting section which selects a light-emitting section supplied with an output signal of the integrated output value control circuit from the first and second light-emitting sections.

According to a third aspect of the present invention, there is provided a light source device according to the second aspect, wherein the integrated output values contain light emission intensities and light emission periods of the first and second light-emitting sections, the light emission periods of the first and second light-emitting sections are synchronized with an exposure period of the image pickup element and at least one of the light emission intensities and light emission periods of the first and second light-emitting sections are independently controlled within the exposure period.

According to a fourth aspect of the present invention, there is provided a light source device according to the third aspect, wherein at least one light-emitting section of the first and second light-emitting sections is caused to emit light with light emission intensity higher than the rated level in a preset period of time.

According to a fifth aspect of the present invention, there is provided a light source device according to the third aspect, wherein the integrated output value control section compares the light emission period with the exposure period of the image pickup element when it is detected in the comparison by the comparator that the reference level is larger than the dimming signal and controls at least one of the light emission intensities and light emission periods of the first and second light-emitting sections based on the comparison result obtained at this time.

According to a sixth aspect of the present invention, there is provided a light source device according to the third or the fifth aspect, wherein the integrated output value control section compares the light emission intensities of the first and second light-emitting sections with a preset value larger than the rated level when it is detected in the comparison by the comparator that the reference level is smaller than the dimming signal and controls the light emission intensities or light emission periods of the first and second light-emitting sections based on the comparison result obtained at this time.

According to a seventh aspect of the present invention, there is provided a light source device according to one of the first to sixth aspects, wherein the first and second light-emitting sections are two LEDs associated with R, G, and B.

According to an eighth aspect of the present invention, there is provided a light source device comprising:

a first light-emitting section which generates illumination light to be applied to a subject, a second light-emitting section which generates illumination light with wavelength different from the illumination light generated from the first light-emitting section, an image pickup element which photographs the subject, a drive signal generating section which generates a drive signal to drive the image pickup element, and an integrated output value control section which independently controls integrated output values of the first light-emitting section and second light-emitting section in synchronism with the drive signal generated from the drive signal generating section.

According to a ninth aspect of the present invention, there is provided a light source device according to the eighth aspect, wherein the integrated output value control section includes a comparator which compares a dimming signal generated based on an image pickup signal from an image pickup element which photographs the subject with a reference level, an integrated output value control circuit which controls the integrated output values of the first and second light-emitting sections based on the comparison result, and a light-emitting section selecting section which selects a light-emitting section supplied with an output signal of the integrated output value control circuit from the first and second light-emitting sections.

According to a tenth aspect of the present invention, there is provided a light source device according to the ninth aspect, wherein the integrated output values contain light emission intensities and light emission periods of the first and second light-emitting sections, the light emission periods of the first and second light-emitting sections are synchronized with an exposure period of the image pickup element and at least one of the light emission intensities and light emission periods of the first and second light-emitting sections are independently controlled within the exposure period.

According to an eleventh aspect of the present invention, there is provided a light source device according to the tenth aspect, wherein at least one light-emitting section of the first and second light-emitting sections is caused to emit light with light emission intensity higher than the rated level in a preset period of time.

According to a twelfth aspect of the present invention, there is provided a light source device according to the tenth aspect, wherein the integrated output value control section compares the light emission period with the exposure period of the image pickup element when it is detected in the comparison by the comparator that the reference level is larger than the dimming signal and controls at least one of the light emission intensities and light emission periods of the first and second light-emitting sections based on the comparison result obtained at this time.

According to a thirteenth aspect of the present invention, there is provided a light source device according to the tenth or twelfth aspect, wherein the integrated output value control section compares the light emission intensities of the first and second light-emitting sections with a preset value larger than the rated level when it is detected in the comparison by the comparator that the reference level is smaller than the dimming signal and controls the light emission intensities or light emission periods of the first and second light-emitting sections based on the comparison result obtained at this time.

According to a fourteenth aspect of the present invention, there is provided a light source device according to the eighth or thirteenth aspect, wherein the first and second light-emitting sections are two LEDs associated with R, G, and B.

BRIEF DESCRIPTION OF DRAWINGS

FIG. 3 is a diagram showing the configuration of a light-emitting diode drive control section 3 and a periphery thereof according to a first embodiment of this invention.

FIG. 4A is a diagram showing the concrete configuration (No. 1) of a light emission/dimming control circuit 71 shown in FIG. 3.

FIG. 4B is a diagram showing the concrete configuration (No. 2) of the light emission/dimming control circuit 71 shown in FIG. 3.

FIG. 4C is a diagram showing the concrete configuration (No. 3) of the light emission/dimming control circuit 71 shown in FIG. 3.

FIG. 5A is a diagram showing an example of the configuration (No. 1) of simultaneously controlling the light emission intensity and light emission period of the light-emitting diode 10.

FIG. 9B is a diagram showing an example of the configuration (No. 2) of simultaneously controlling the light emission intensity and light emission period of the light-emitting diode 10.

FIG. 14 is a diagram for illustrating a modification of the embodiment for simultaneously controlling the light emission intensity and light emission period of the light-emitting diode 10.

FIG. 16 is a diagram showing the state in which the light emission periods of the R, G, and B light-emitting diodes 10-1 to 10-3 are independently changed.

FIG. 17 is a diagram showing the state in which the light emission intensities and light emission periods of the R, G, and B light-emitting diodes 10-1 to 10-3 are independently changed.

FIG. 18 is a diagram showing a modification (controlling the light emission intensity to be set between k times and j times the rated level) of the dimming control shown in FIG. 17.

BEST MODE FOR CARRYING OUT THE INVENTION

Figure 1:
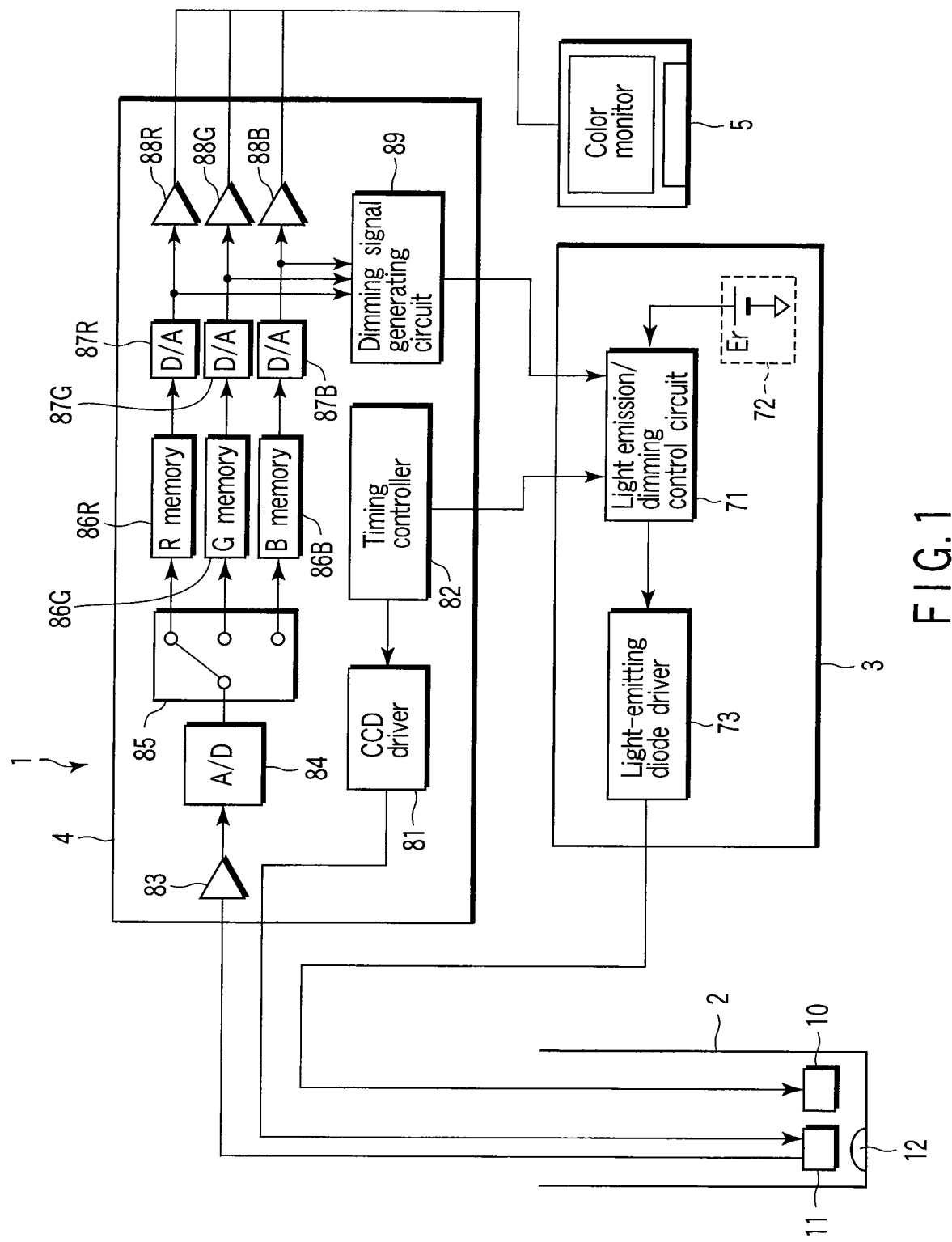
FIG. 1 is a diagram showing the configuration of a field-sequential endoscopic device 1 according to one embodiment of this invention.

There will now be described embodiments of this invention with reference to the drawings. FIG. 1 is a diagram showing the configuration of a field-sequential endoscopic device 1 according to one embodiment of this invention. The present configuration includes an electronic endoscope 2 having a light-emitting diode 10 as a light-emitting section, a light-emitting diode drive control section 3 which controls the driving of the light-emitting diode 10, a video processor 4 as a signal processing device which performs a signal process for an image signal acquired by the electronic endoscope 2, and a color monitor 5 which displays the image signal processed by the video processor 4. The electronic endoscope 2, light-emitting diode drive control section 3, video processor 4 and color monitor 5 are connected via signal lines or the like. Further, in FIG. 1, only one light-emitting diode 10 is shown, but in practice, three diodes are arranged for red (R), green (G), and blue (B). The details are described later. Further, in the present embodiment, a case wherein three light-emitting diodes for R, G, and B are used is explained, but the point of this invention is to independently control a plurality of light-emitting diodes. Therefore, if at least two light-emitting diodes are provided, this invention can be realized.

With the above configuration, the light-emitting diode 10 is caused to emit light and illuminate the subject (not shown). An optical image of the illuminated subject is formed on a CCD 11 as an image pickup element arranged on the focal plane by use of an objective optical system 12 in the electronic endoscope 2. The optical image is photoelectrically converted by the CCD 11 and stored as a signal charge.

When a CCD drive signal is applied to the CCD 11 from a CCD driver 81 in the video processor 4, the signal charge stored in the CCD 11 is transferred and output to the exterior as an image pickup signal output.

The output signal of the CCD 11 is amplified by a preamplifier 83 in the video processor 4 and then digitized by an analog-to-digital converter 84. The R, G, and B image pickup signals converted into digital data are stored in R, G, and B memories 86R, 86G, 86B by switching a selector 85 in synchronism with field-sequential illumination.

The image pickup data stored in R, G, and B memories 86R, 86G, 86B are simultaneously read, respectively converted into analog signals by digital-to-analog converters 87R, 87G, 87B and are set as R, G, and B signals. The R, G, and B signals are output to the color monitor 5 together with a sync signal which is not shown in the drawing via buffers 88R, 88G, 88B and a subject image is displayed in color on the display screen thereof.

Further, the R, G, and B signals output via the digital-to-analog converters 87R, 87G, 87B are input to a dimming signal generating circuit 89 and a dimming signal obtained by integration for, for example, one field period is generated. The dimming signal is input to a light emission/dimming control circuit 71 of the light-emitting diode drive control section 3.

Reference voltage Er is applied to the light-emission/dimming control circuite 71 from a reference level generating circuit 72 which generates a reference level corresponding to brightness suitable for observation. The reference level can be made variable. The light-emission/dimming control circuit 71 compares the reference voltage Er with an input dimming signal to generate a difference signal. The light emission intensity and light emission period of the light-emitting diode 10 can be varied by outputting a light-emission/dimming signal which causes the difference signal to be set to "0" to the light-emitting diode driver 73.

Figure 2:
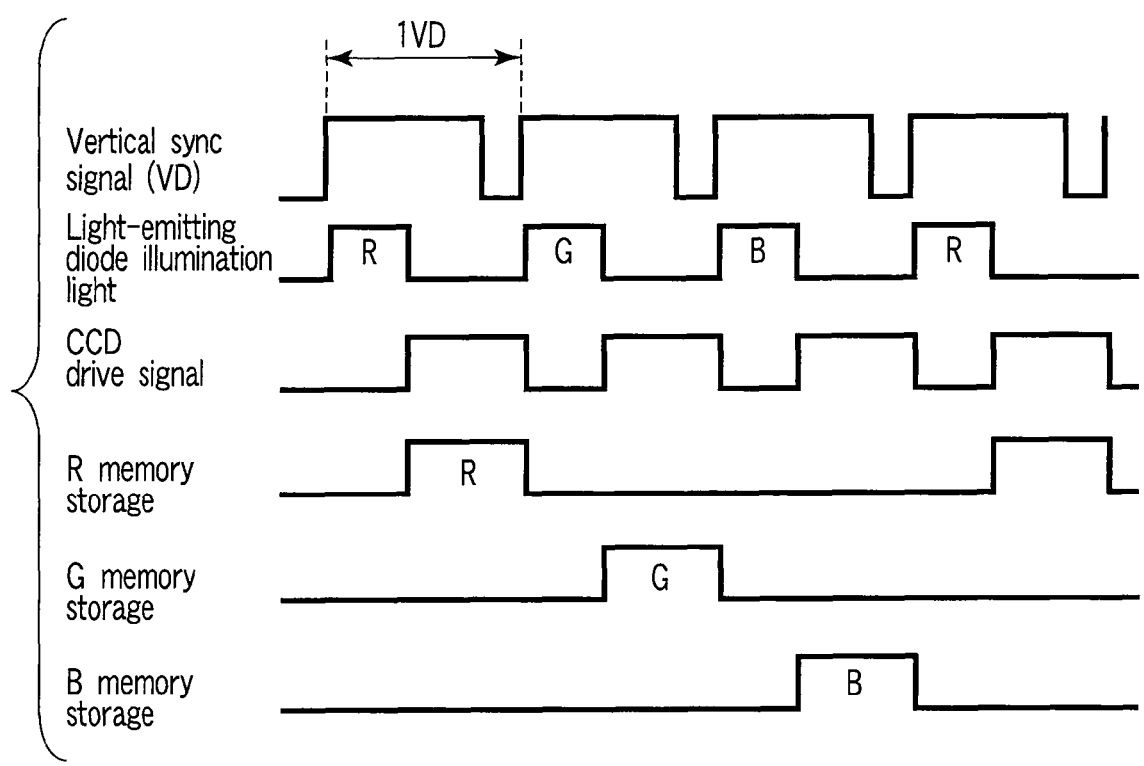
FIG. 2 is a timing chart showing the relation between timings of the operations of lighting a light-emitting diode 10, driving a CCD 11 and storing an image pickup signal.

FIG. 2 is a timing chart showing the relation between timings of the operations of lighting the light-emitting diode 10, driving the CCD 11 and storing the image pickup signal. A timing controller 82 is driven by a vertical sync signal (VD) generated by a sync signal generation circuit which is not shown in the drawing. Operation timings of the CCD driver 81 and light-emission/dimming control circuit 71 are determined by an output signal from the timing controller 82.

That is, the light-emission/dimming control circuit 71 outputs a light-emitting diode drive signal to the light-emitting diode driver 73 in synchronism with the output signal from the timing controller 82. The light-emitting diode driver 73 causes the light-emitting diode 10 to emit light in the order of R, G, and B in synchronism with the light-emitting diode drive signal. The light emission/dimming control operation of the light-emitting diode 10 is performed based on the reference voltage generated by the reference level generating circuit 72, but the details are explained later.

The CCD driver 81 outputs a CCD drive signal to the CCD 11 in synchronism with the output signal from the timing controller 82 after the light emission periods of R, G, and B. As a result, the CCD 11 is driven and the image pickup operation is performed. Image pickup signals acquired by the image pickup operation are stored in the R, G, and B memories 86R, 86G, 86B according to a switching operation of the selector 85. The operations of causing the R, G, and B light-emitting diodes 10 to each emit light, driving the CCD 11 and storing the image pickup signals are performed in one VD period indicating separation of two image screens.

FIG. 3 shows the configuration of the light-emitting diode drive control section 3 and the periphery thereof according to a first embodiment of this invention. In FIG. 3, three light-emitting diodes 10-1, 10-2, 10-3 are arranged for R, G, and B as the light-emitting diode 10 and light-emitting diode drivers 73-1, 73-2, 73-3 are arranged to drive the respective light-emitting diodes 10-1, 10-2, 10-3 and connected to the light19 emission/dimming control circuit 71.

FIGS. 4A, 4B, 4C show the concrete configuration of the light emission/dimming control circuit 71 shown in FIG. 3. FIG. 4A shows the first concrete configuration for independently controlling integrated output values of the light-emitting diodes 10-1, 10-2, 10-3. The configuration includes a comparator 71-1 which compares a dimming signal from the dimming signal generating circuit 89 with the reference voltage from the reference level generating circuit 72 based on a comparison timing signal from the timing controller 82, an integrated output value control circuit 71-2 which controls an integrated output value (for example, the total light amount in the exposure period) of the light-emitting diode 10 according to the comparison result at this time, and an RGB switching circuit 71-3 which switches the light-emitting diode driver to be driven based on an RGB switching signal from the timing controller 82.

FIG. 4B shows the second concrete configuration. The configuration is similar to the first concrete configuration except that a light emission intensity control circuit 71-4 which controls the light emission intensity of the light-emitting diode 10 is arranged as one example of the integrated output value control circuit 71-2 in the first concrete configuration.

FIG. 4C shows the third concrete configuration. The configuration is similar to the first concrete configuration except that a light emission period control circuit 71-5 which controls the light emission period of the light-emitting diode 10 is arranged as one example of the integrated output value control circuit 71-2 in the first concrete configuration.

Figure 5B:
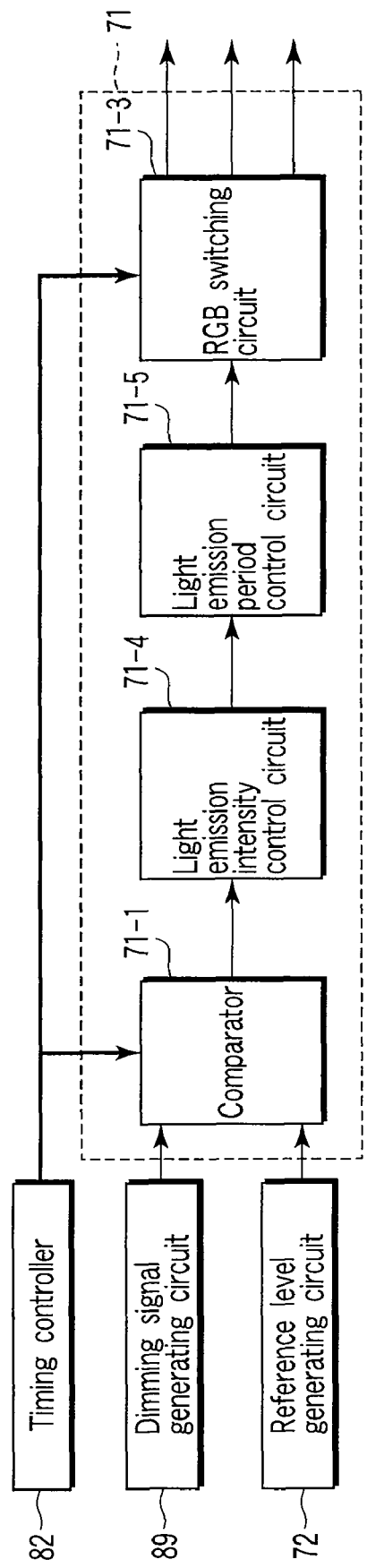
FIG. 5B is a diagram showing an example of the configuration (No. 2) of simultaneously controlling the light emission intensity and light emission period of the light-emitting diode 10.
Figure 5C:
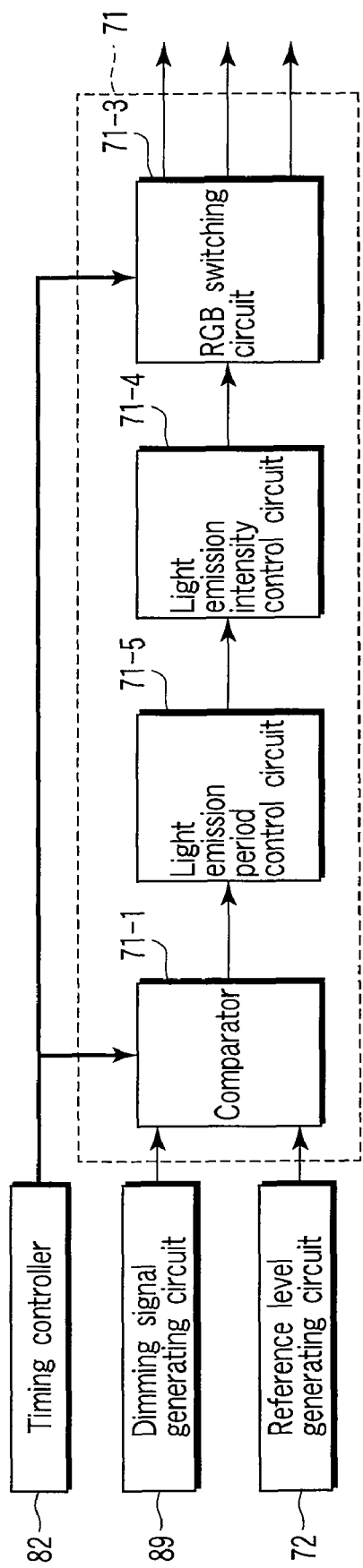
FIG. 5C is a diagram showing an example of the configuration (No. 3) of simultaneously controlling the light emission intensity and light emission period of the light-emitting diode 10.

FIG. 5A to FIG. 5C show examples of the configuration of simultaneously controlling the light emission intensity and light emission period of the light-emitting diode 10 as the fourth concrete configuration. In FIG. 5A, as one example of the integrated output value control circuit 71-2, a light emission intensity control circuit 71-4 and light emission period control circuit 71-5 are arranged in parallel between the comparator 71-1 and the RGB switching circuit 71-3. In FIG. 5B, a light emission intensity control circuit 71-4 and light emission period control circuit 71-5 are serially arranged in this order between the comparator 71-1 and the RGB switching circuit 71-3. In FIG. 5C, a light emission period control circuit 71-5 and light emission intensity control circuit 71-4 are serially arranged in this order between the comparator 71-1 and the RGB switching circuit 71-3.

Figure 6:
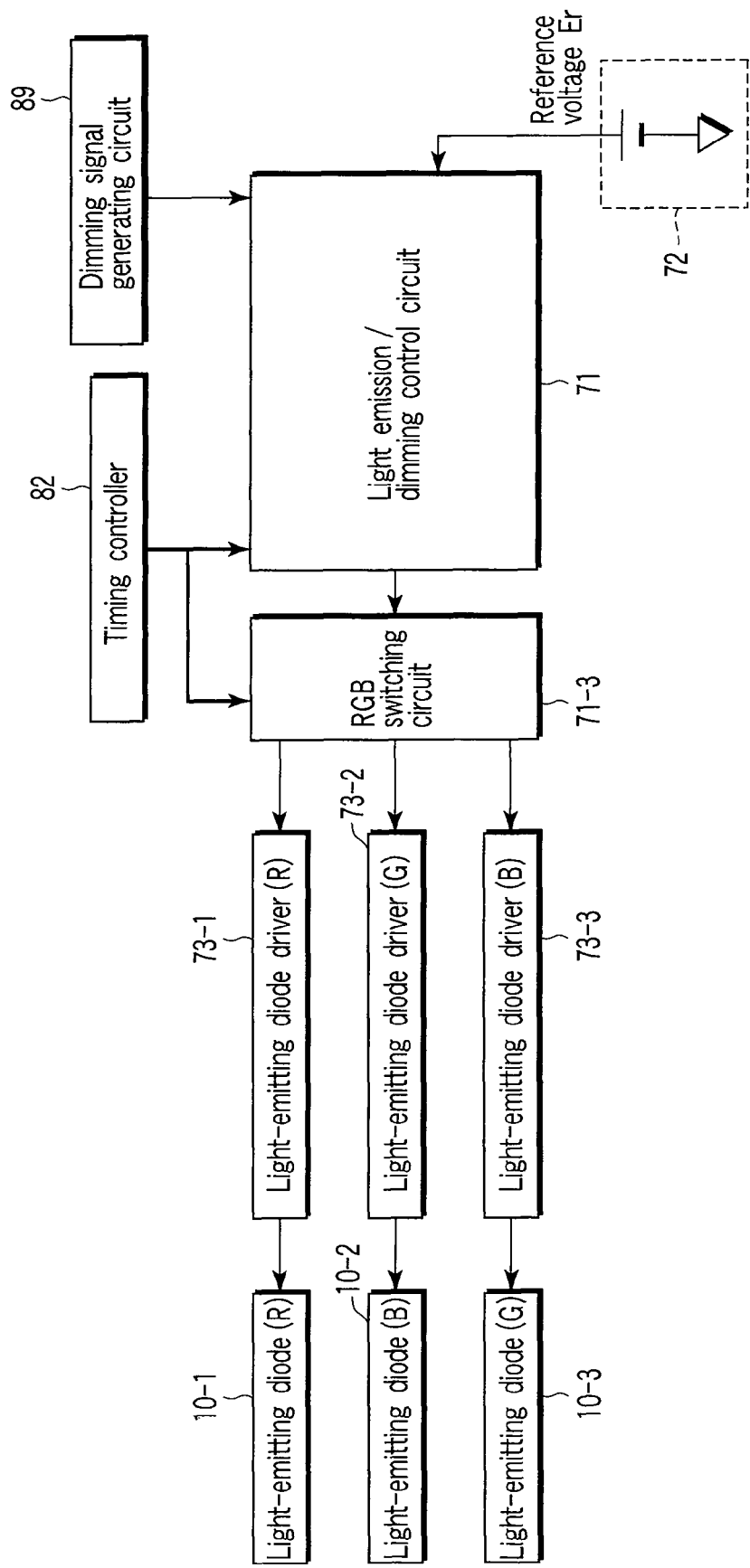
FIG. 6 is a diagram showing the configuration of a light-emitting diode drive control section 3 and a periphery thereof according to a second embodiment of this invention.

FIG. 6 shows the configuration of a light-emitting diode drive control section 3 and the periphery thereof according to a second embodiment of this invention. This case is characterized in that an RGB switching circuit 71-3 is arranged outside a light emission/dimming control circuit 71. The RGB switching circuit 71-3 switches a light-emitting diode driver to be driven based on an RGB switching signal from a timing controller 82. With the above configuration, integrated output values of light-emitting diodes 10-1, 10-2, 10-3 can be independently controlled.

Figure 7:
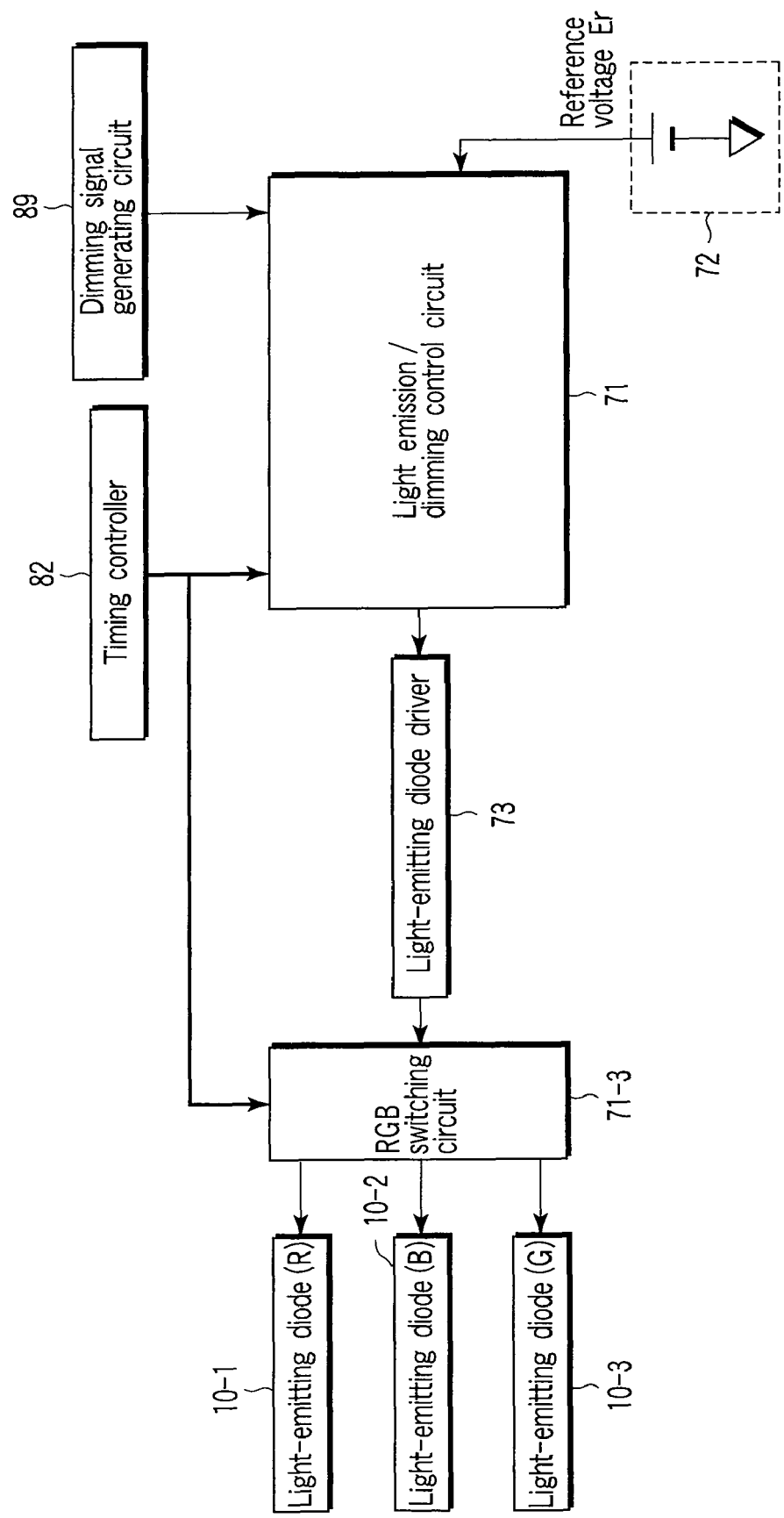
FIG. 7 is a diagram showing the configuration of a light-emitting diode drive control section 3 and a periphery thereof as a modification of the second embodiment of this invention.

FIG. 7 shows the configuration of a light-emitting diode drive control section 3 and the periphery thereof as a modification of the second embodiment of this invention. This case is characterized in that the RGB switching circuit 71-3 is arranged outside the light emission/dimming control circuit 71 with the light-emitting diode driver 73 disposed therebetween. The RGB switching circuit 71-3 switches a light-emitting diode to be driven based on the RGB switching signal from the timing controller 82. With the above configuration, it is not necessary to arrange the light-emitting diode driver 73 for each of R, G, and B and it is sufficient to use one driver.

Figure 8A:
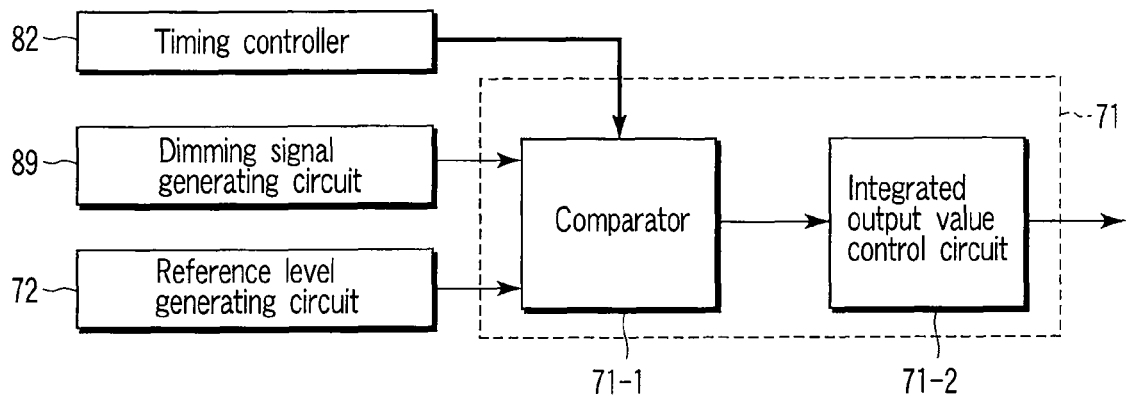
FIG. 8A is a diagram showing the concrete configuration (No. 1) of a light emission/dimming control circuit 71 shown in FIG. 6 and FIG. 7.
Figure 8B:
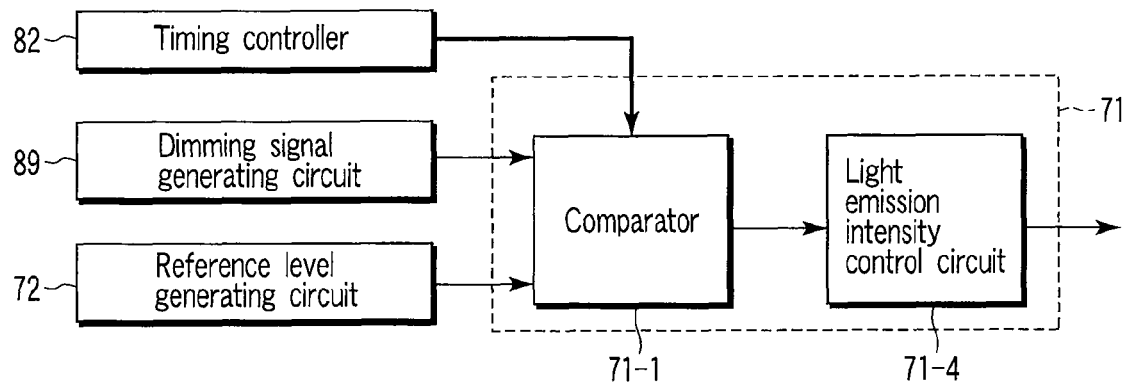
FIG. 8B is a diagram showing the concrete configuration (No. 2) of the light emission/dimming control circuit 71 shown in FIG. 6 and FIG. 7.
Figure 8C:
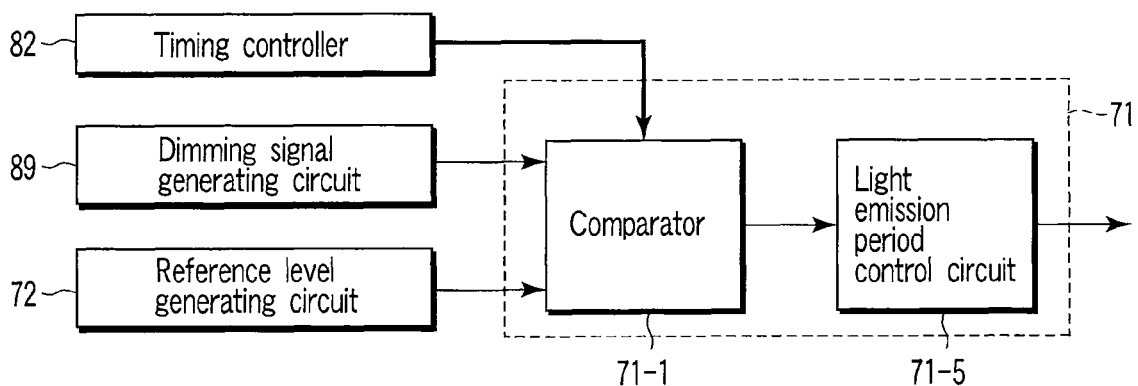
FIG. 8C is a diagram showing the concrete configuration (No. 3) of the light emission/dimming control circuit 71 shown in FIG. 6 and FIG. 7.

FIGS. 8A, 8B, 8C show the concrete configurations of the light emission/dimming control circuit 71 shown in FIG. 6 and FIG. 7. FIG. 8A shows the first concrete configuration. The configuration includes a comparator 71-1 which compares a dimming signal from the dimming signal generating circuit 89 and reference voltage from the reference level generating circuit 72 based on a comparison timing signal from the timing controller 82 and an integrated output value control circuit 71-2 which controls an integrated output value of the light-emitting diode 10 according to the comparison result at this time.

FIG. 8B shows the second concrete configuration. The configuration is similar to the first concrete configuration except that a light emission intensity control circuit 71-4 which controls the light emission intensity of the light-emitting diode 10 is arranged as one example of the integrated output value control circuit 71-2 in the first concrete configuration.

FIG. 8C shows the third concrete configuration. The configuration is similar to the first concrete configuration except that a light emission period control circuit 71-5 which controls the light emission period of the light-emitting diode 10 is arranged as one example of the integrated output value control circuit 71-2 in the first concrete configuration.

Figure 9A:
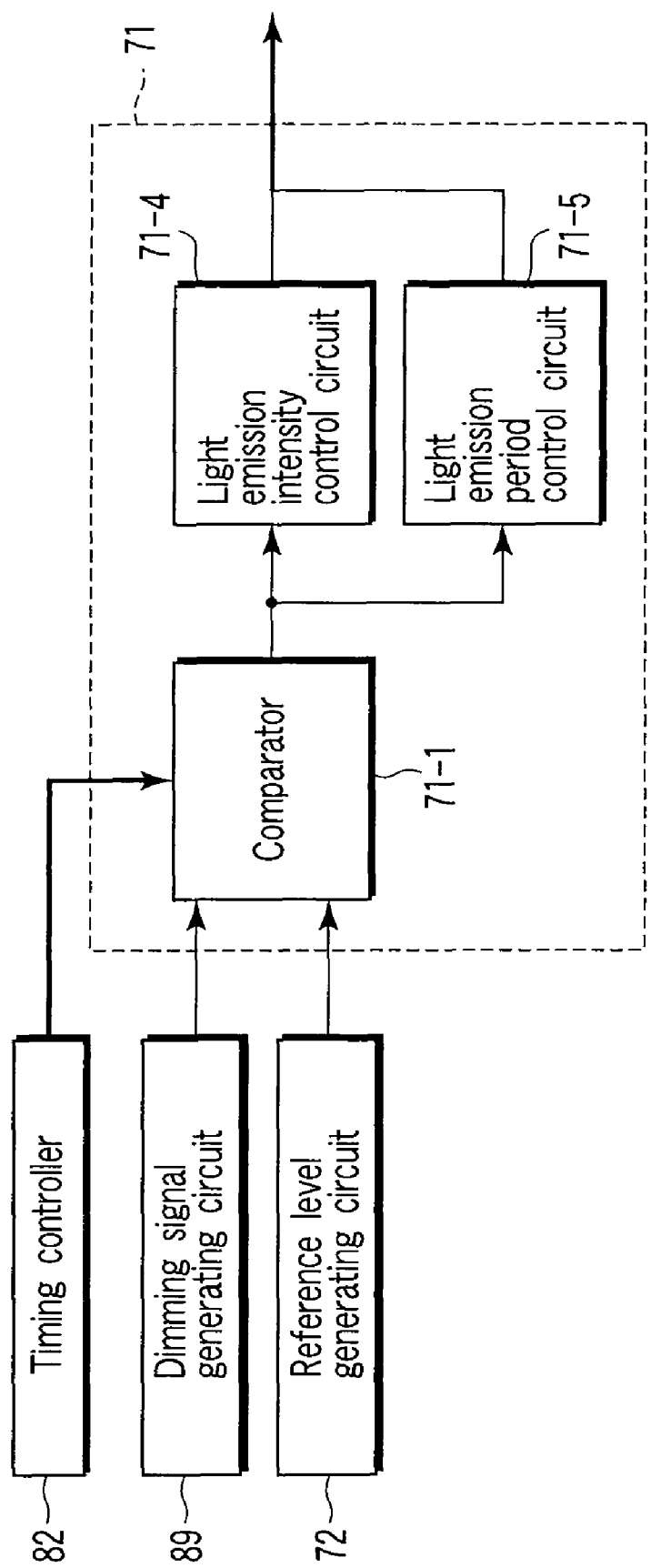
FIG. 9A is a diagram showing an example of the configuration (No. 1) of simultaneously controlling the light emission intensity and light emission period of the light-emitting diode 10.
Figure 9C:
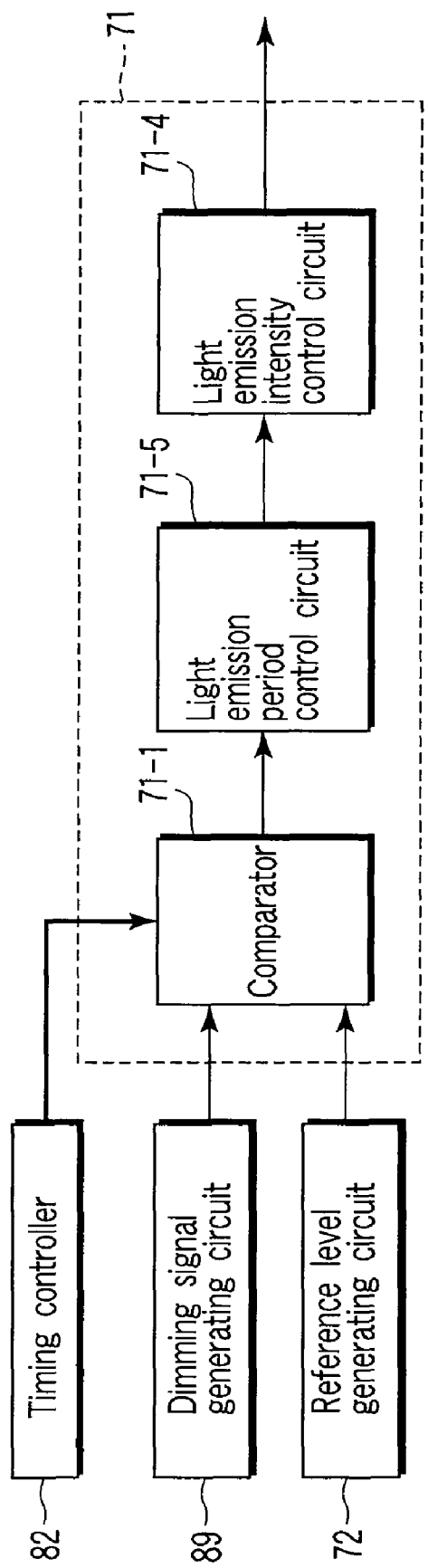
FIG. 9C is a diagram showing an example of the configuration (No. 3) of simultaneously controlling the light emission intensity and light emission period of the light-emitting diode 10.

FIG. 9A to FIG. 9C show examples of the configuration of simultaneously controlling the light emission intensity and light emission period of the light-emitting diode 10. In FIG. 9A, a light emission intensity control circuit 71-4 and light emission period control circuit 71-5 are arranged in parallel between the comparator 71-1 and the RGB switching circuit 71-3. In FIG. 9B, a light emission intensity control circuit 71-4 and light emission period control circuit 71-5 are serially arranged in this order between the comparator 71-1 and the RGB switching circuit 71-3. In FIG. 9C, a light emission period control circuit 71-5 and light emission intensity control circuit 71-4 are serially arranged in this order between the comparator 71-1 and the RGB switching circuit 71-3.

Next, the details of light emission/dimming control of the light-emitting diode according to the present embodiment are explained. A certain type of CCD has an exposure period which is a period in which light is applied to generate charges by photoelectrical conversion and store the same and a light blocking period in which light is blocked and prevented from being made incident thereon when the stored charges are read.

The present embodiment is characterized in that the light-emitting diode is lit in the exposure period among the above two periods, but the light-emitting diode is turned off in the light blocking period and the light-emitting diode is lit not only at the rated level but also at a level higher than the rated level in the exposure period.

Figure 10:
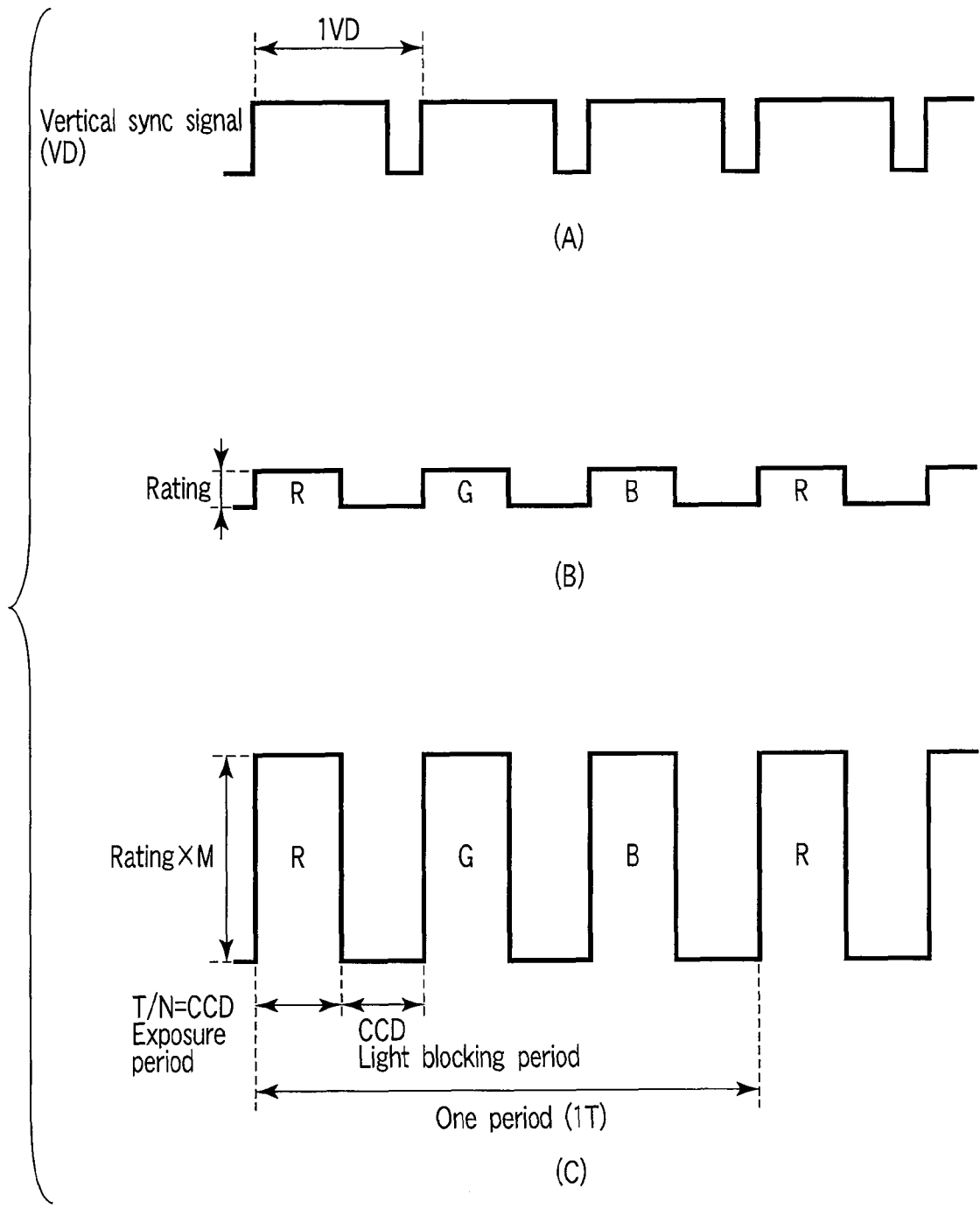
FIG. 10 is a diagram showing the state when light-emitting diodes 10-1 to 10-3 are sequentially lit at the rated level or at a level higher than the rated level.

(A) to (C) of FIG. 10 show the states when the light-emitting diodes 10-1 to 10-3 are sequentially lit at the rated level or at a level higher than the rated level. (A) of FIG. 10 indicates a vertical sync signal (VD), (B) of FIG. 10 indicates a case where the light-emitting diodes 10-1 to 10-3 are sequentially driven at the rated level for R, G, and B in synchronism with the timing of the exposure period of the CCD 11 and an example of (C) of FIG. 10 indicates a case where the light-emitting diodes 10-1 to 10-3 are driven at M (M: positive real number) times the rated level in synchronism with the timing of the exposure period of the CCD 11.

Since the light-emitting diodes 10-1 to 10-3 emit light only in the exposure period, the lighting time becomes ⅙ times one period (1T) for R, G, and B, respectively, in the example of (C) of FIG. 10. Therefore, the power consumption when light is emitted only in the exposure period becomes ⅙ the power consumption when the light-emitting diode is kept lit at the rated level for R, G, and B, respectively. As a result, if light is emitted only in the exposure period and even if it is lit at six times the rated level, the power consumption at this time becomes approximately equal to that when it is kept lit at the rated level. Thus, an endoscopic image which is approximately six times brighter than that at the driving time at the rated level can be obtained.

Next, the procedure of controlling the integrated output value of the light-emitting diode 10 is explained. Since the control method can be attained by use of the same procedure for the light-emitting diodes 10-1 to 10-3 for R, G, and B, the procedure only for the light-emitting diode 10-1 for R is explained in this example.

Figure 11:
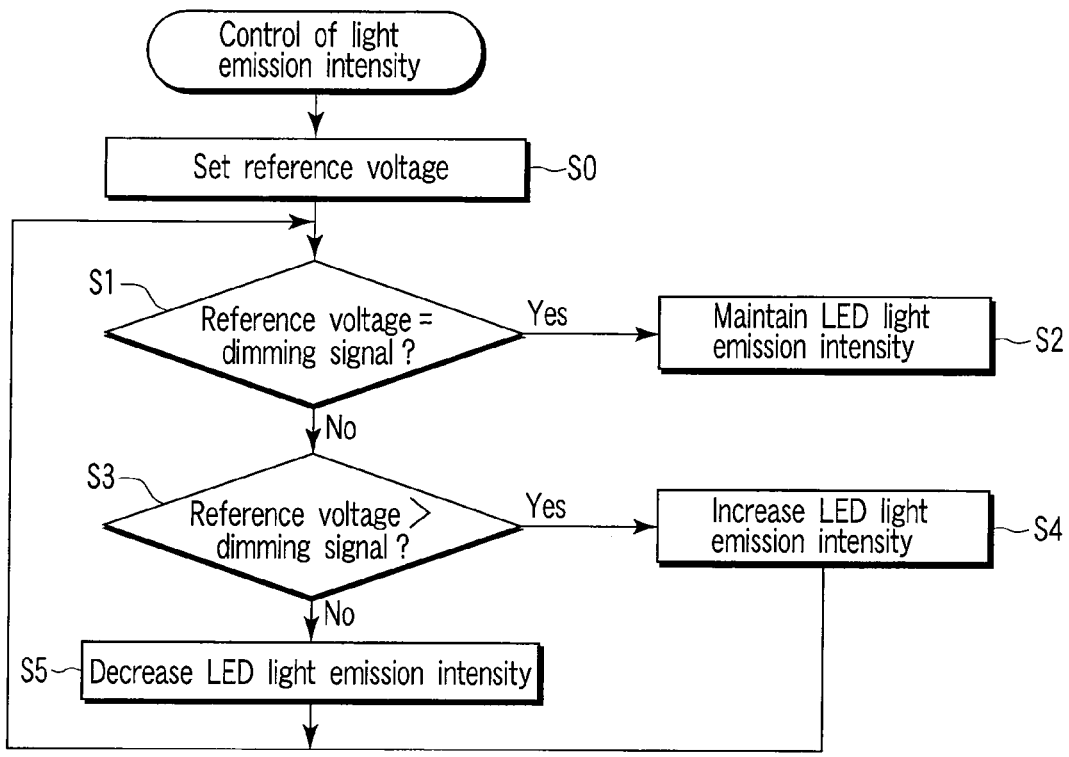
FIG. 11 is a diagram for illustrating the procedure of controlling the light emission intensity of the light-emitting diode 10.

FIG. 11 is a diagram for illustrating the procedure of controlling the light emission intensity of the light-emitting diode 10-1 for R.

First, reference voltage Er is set (step S0), the set reference voltage Er is compared with a dimming signal from the dimming signal generation circuit 89 and whether or not the reference voltage Er is equal to the dimming signal is determined (step S1). When the result of determination is "YES", the present light emission intensity of the light-emitting diode 10-1 for R is maintained without changing a value of M (M: positive real number) expressing a multiple of the rated level (step S2). Further, when the determination in step S1 is "NO", whether or not the reference voltage Er is larger than the dimming signal is determined (step S3), and if it is "YES", the LED light emission intensity is increased by making the value of M larger than the present value (step S4). After this, the process returns to step S1. Further, if the determination in step S3 is "NO", the LED light emission intensity is decreased by making the value of M smaller than the present value (step S5). After this, the process returns to step S1.

According to the above method, since the light emission intensity of the light-emitting diode 10 can be controlled to always set the reference voltage Er and dimming signal equal to each other, an endoscopic image suitable for observation can always be obtained.

Figure 12:
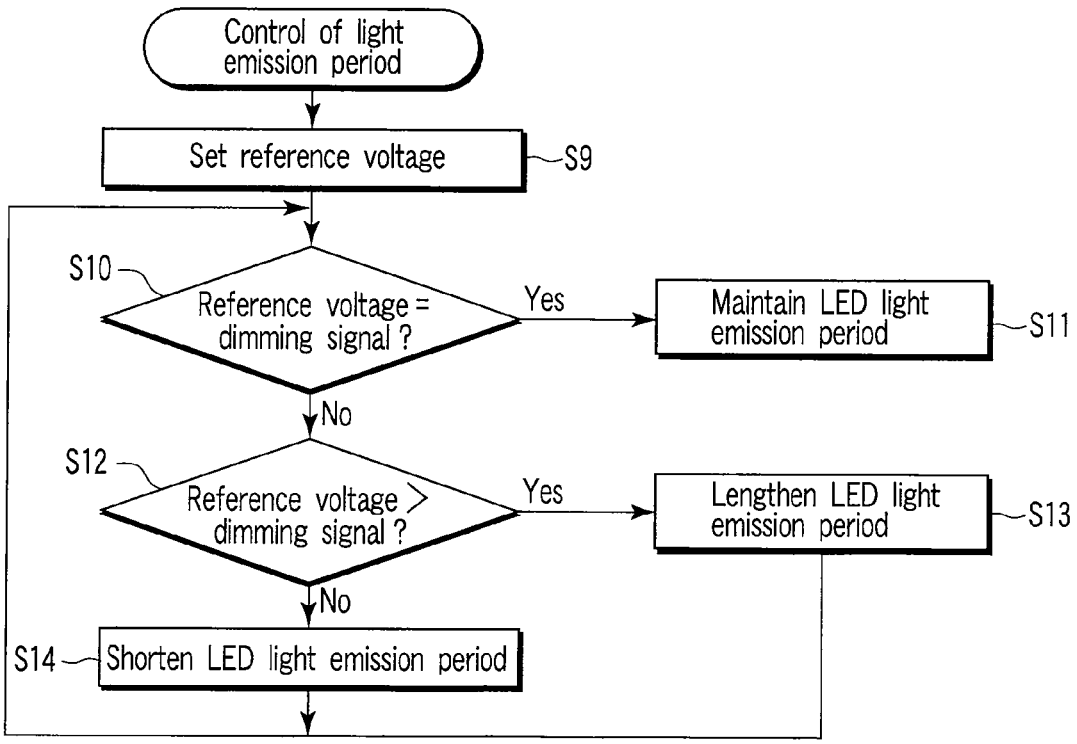
FIG. 12 is a diagram for illustrating the procedure of controlling the light emission period of the light-emitting diode 10.

Next, the procedure of controlling the light emission period of the light-emitting diode 10-1 for R is explained with reference to FIG. 12. Such a control operation can be realized by the configuration shown in FIG. 4(C), for example.

First, reference voltage Er is set (step S9) and the set reference voltage Er is compared with a dimming signal from the dimming signal generating circuit 89 by the comparator 71-1 to determine whether or not the reference voltage Er is equal to the dimming signal (step S10). When the determination result is "YES", the present light emission period of the light-emitting diode 10-1 is maintained (step S11). Further, if the determination in step S10 is "NO", whether or not the reference voltage Er is larger than the dimming signal is determined (step S12). When the determination in this step is "YES", the light emission period of the light-emitting diode 10-1 is set longer than the present value (step S13) and then the process returns to step S10. Further, if the determination in step S12 is "NO", the light emission period of the light-emitting diode 10-1 is set shorter than the present value (step S14) and, after this, the process returns to step S10.

According to the above method, since the light emission period of the light-emitting diode 10-1 can be controlled to always set the reference voltage Er and dimming signal equal to each other, an endoscopic image suitable for observation can always be obtained.

Figure 13:
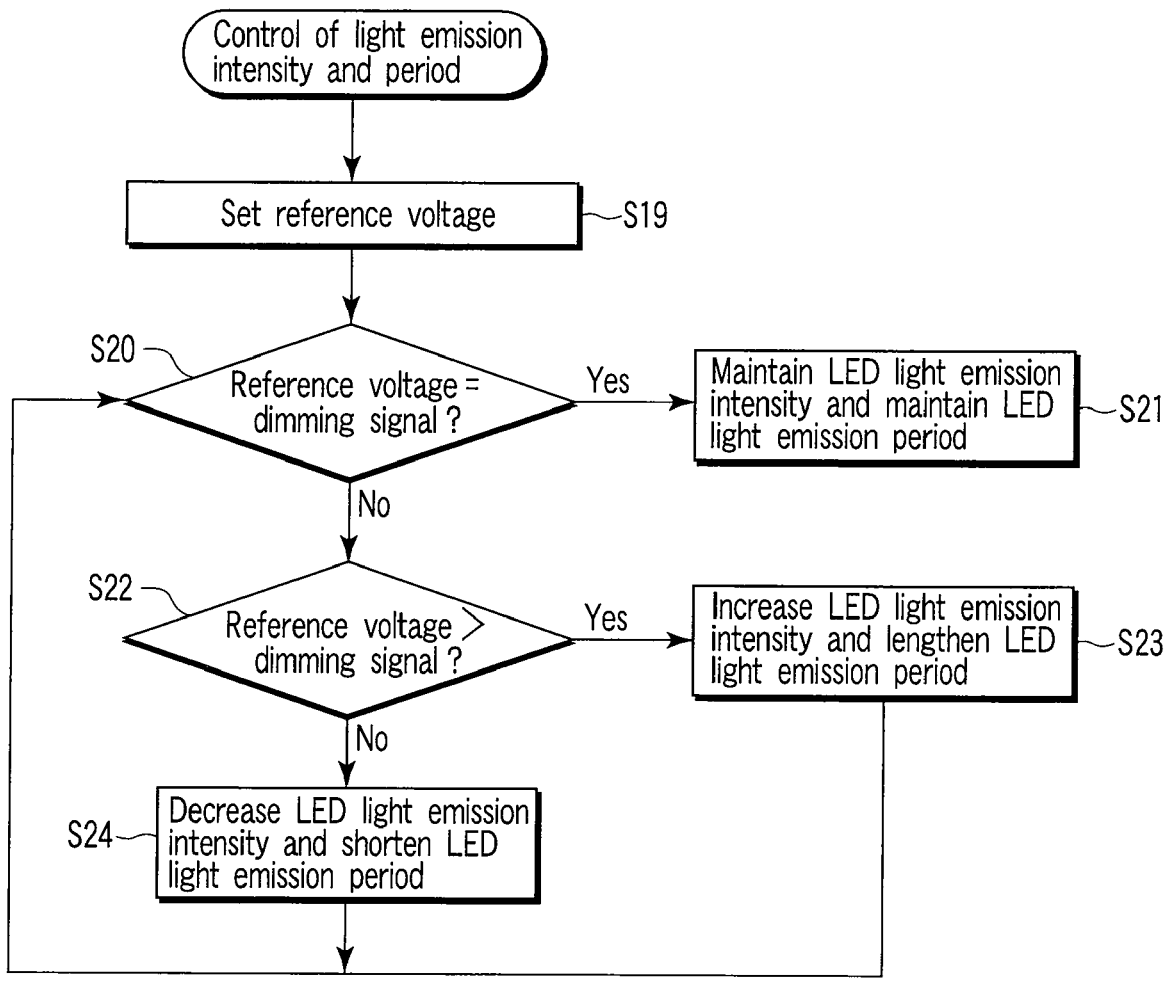
FIG. 13 is a diagram for illustrating the procedure of simultaneously controlling the light emission intensity and light emission period of the light-emitting diode 10.

Next, the procedure of simultaneously controlling the light emission intensity and light emission period of the light-emitting diode 10-1 for R is explained with reference to FIG. 13. Such a control operation can be realized by the configuration shown in FIG. 5(A), for example.

First, reference voltage Er is set (step S19) and the set reference voltage Er is compared with a dimming signal from the dimming signal generating circuit 89 by the comparator 71-1 to determine whether or not the reference voltage Er is equal to the dimming signal (step S20). When the determination result is "YES", the present light emission intensity and light emission period of the light-emitting diode 10-1 are maintained (step S21). Further, if the determination in step S20 is "NO", whether or not the reference voltage Er is larger than the dimming signal is determined (step S22). When the determination in this step is "YES", the light emission intensity of the light-emitting diode 10-1 is increased and at the same time the light emission period is set longer than the present value (step S23). After this, the process returns to step S20. Further, if the determination in step S22 is "NO", the light emission intensity of the light-emitting diode 10-1 is decreased and at the same time the light emission period is set shorter than the present value (step S24). After this, the process returns to step S20.

According to the above method, since the light emission period of the light-emitting diode 10-1 can be controlled to always set the reference voltage Er and dimming signal equal to each other, an endoscopic image suitable for observation can always be obtained. Further, at the dimming time, since the light emission intensity and light emission period of the light-emitting diode 10 are simultaneously controlled, an advantage that the dimming speed can be increased and the dimming range can be enlarged can be provided.

Next, a modification of the embodiment (FIG. 13) in which the light emission intensity and light emission period of the light-emitting diode 10-1 are simultaneously controlling is explained with reference to FIG. 14. In this modification, when the dimming signal is smaller than the reference voltage, a control operation is performed to increase the light emission intensity or set the light emission period longer. That is, the light emission period is compared with the CCD exposure period and since the light emission period cannot be lengthened any more if the light emission period is equal to the CCD exposure period, only the light emission intensity is increased while the present light emission period is maintained. Further, since the light emission period can be made further longer if the light emission period is shorter than the CCD exposure period, not only the light emission intensity is increased but also the light emission period is lengthened.

On the other hand, if the dimming signal is larger than the reference voltage, a control operation is performed to decrease the light emission intensity or shorten the light emission period. That is, the light emission intensity is compared with a value which is j (j: positive real number) times the rated level and if the light emission intensity is larger than j times the rated level, only the light emission intensity is decreased while the light emission period is maintained. Further, if the light emission intensity is equal to j times the rated level, only the light emission period is shortened while the light emission intensity is maintained.

Such a control operation is realized by the configuration shown in FIG. 5A, for example.

In FIG. 14, first, reference voltage Er is set (step S29) and the set value is compared with a dimming signal from the dimming signal generating circuit 89 by the comparator 71-1 to determine whether or not the reference voltage Er is equal to the dimming signal (step S30). When the determination result is "YES", the present light emission intensity and light emission period of the light-emitting diode 10-1 are maintained (step S31). Further, if the determination in step S30 is "NO", whether or not the reference voltage Er is larger than the dimming signal is determined (step S32). When the determination in this step is "YES", the present light emission period of the light-emitting diode 10-1 is compared with preset exposure time of the CCD 11 (step S33). In this case, if the light emission period of the light-emitting diode 10-1 is equal to the exposure time of the CCD 11, the light emission intensity of the light-emitting diode 10-1 is increased (step S34) while the present light emission period is maintained. After this, the process returns to step S30. Further, if the light emission period of the light-emitting diode 10-1 is shorter than the exposure period of the CCD 11, the light emission intensity is increased and at the same time the light emission period is lengthened (step S36). After this, the process returns to step S30.

When the determination in step S32 is "NO", the present light emission intensity is compared with a value of j times the rated level (step S35). In this case, if the present light emission intensity is larger than j times the rated level, the light emission intensity of the light-emitting diode 10-1 is decreased (step S37) while the present light emission period is maintained. After this, the process returns to step S30. Further, if the present light emission intensity is equal to j times the rated level, the present light emission intensity is maintained and at the same time the light emission period is shortened (step S38). After this, the process returns to step S30.

According to the above control method, since the light emission period and light emission intensity of the light-emitting diode 10-1 are controlled to always set the reference voltage Er and dimming signal equal to each other, an endoscopic image suitable for observation can always be obtained. Further, if a control operation is performed to decrease the light emission intensity of the light-emitting diode 10-1 to a certain given value (the light emission intensity before the color temperature of the light-emitting diode 10-1 is decreased), the color temperature can be prevented from being decreased due to a decrease in the light emission intensity of the light-emitting diode 10-1.

Figure 15:
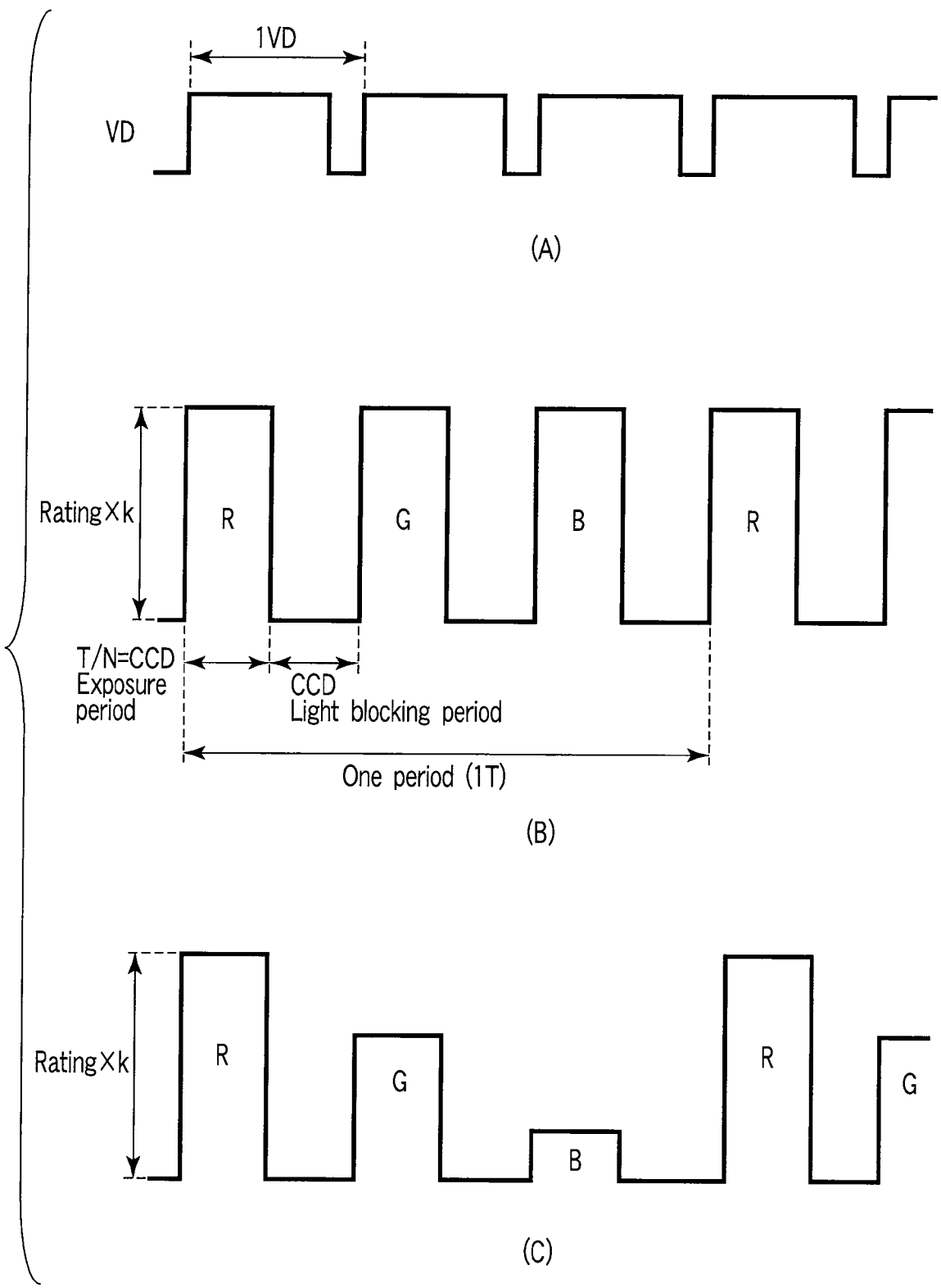
FIG. 15 is a diagram showing the state in which the light emission intensities of the R, G, and B light-emitting diodes 10-1 to 10-3 are independently changed.

(A) to (C) of FIG. 15 show the states in which the light emission intensities of the light-emitting diodes 10-1 to 10-3 for R, G, and B are controlled. (A) of FIG. 15 indicates a vertical sync signal (VD), (B) of FIG. 15 shows the state in which the light-emitting diodes 10-1 to 10-3 each emit light at k (k: positive real number) times the rated level and (C) of FIG. 15 shows the state in which the light emission intensities of the light-emitting diodes 10-1 to 10-3 are independently changed.

(A) to (C) of FIG. 16 show the states in which the light emission periods of the light-emitting diodes 10-1 to 10-3 for R, G, and B are controlled. (A) of FIG. 16 indicates a vertical sync signal (VD), (B) of FIG. 16 shows the state in which the light-emitting diodes 10-1 to 10-3 each emit light at k (k: positive real number) times the rated level and (C) of FIG. 16 shows the state in which the light emission periods of the light-emitting diodes 10-1 to 10-3 are independently changed.

(A) to (C) of FIG. 17 show the states in which the light emission intensities and light emission periods of the light-emitting diodes 10-1 to 10-3 for R, G, and B are controlled. (A) of FIG. 17 indicates a vertical sync signal (VD), (B) of FIG. 17 shows the state in which the light-emitting diodes 10-1 to 10-3 each emit light at k (k: positive real number) times the rated level and (C) of FIG. 17 shows the state in which the light emission intensities and light emission periods of the light-emitting diodes 10-1 to 10-3 are independently changed.

(A) to (C) of FIG. 18 show a modification of (A) to (C) of FIG. 17. (A) of FIG. 18 indicates a vertical sync signal (VD) and (B) of FIG. 18 shows the state in which the light-emitting diodes 10-1 to 10-3 each emit light at k (k: positive real number) times the rated level.

Further, (C) of FIG. 18 shows the state in which the light emission intensities and light emission periods of the light-emitting diodes 10-1 to 10-3 for R, G, and B are changed in a preset range. In this case, the light emission intensities of the light-emitting diodes 10-1 to 10-3 are controlled to be set between k (k: positive real number) times the rated level (in the drawing, the light-emitting diode 10-1 for R) and j (j: positive real number and k>j) times the rated level (in the drawing, the light-emitting diode 10-2 for G). When it is desired to set the integrated output value (total light amount) in the CCD exposure period further smaller than j times the rated level, the light emission period may be shortened instead of reducing the light emission intensity (in the drawing, the light-emitting diode 10-3 for B).

As described above, according to the present embodiment, since the light emission intensities and/or periods of the light-emitting diodes for R, G, and B are independently controlled according to a subject, the subject can be observed with the coloring most suitable for the subject. Further, according to the present embodiment, since the light-emitting diode is lit with the light emission intensity equal to or higher than the rated level, a subject image with sufficient brightness can be obtained.

In the present embodiment, the light-emitting diode is used as the light-emitting element as the illuminating section, but a laser diode can also be used. In the present embodiment, the CCD is used as an image pickup element, a CMOS device can also be used. Further, the light-emitting element as the illuminating section is arranged on the head of the electronic endoscope 2, but it may be arranged within the light-emitting diode drive control section 3, the operating portion (not shown) of the electronic endoscope 2 or the like. Further, in the present embodiment, the light-emitting diode drive control section 3 is separately arranged, but it can be arranged within the video processor 4, on the head of the electronic endoscope 2 or on the operating portion (not shown) of the electronic endoscope 2 which is not shown in the drawing or the like. Further, for example, the R, G, and B light-emitting elements are used for complementary color illumination to sequentially illuminate R and G, G and B, B and R.

INDUSTRIAL APPLICABILITY

According to this invention, the subject can be observed with the coloring most suitable for the subject.

Further, according to this invention, a subject image with sufficient brightness can be obtained.

The invention claimed is:
1. A light source device comprising:
a first light-emitting section which generates illumination light to be applied to a subject, a second light-emitting section which generates illumination light with wavelength different from the illumination light generated from the first light-emitting section, and
an integrated output value control section which independently controls integrated output values of the first light-emitting section and second light-emitting section in synchronism with image pickup timing at which the subject is photographed,
wherein the integrated output value control section includes a comparator which compares a dimming signal generated based on an image pickup signal from an image pickup element which photographs the subject with a reference level, an integrated output value control circuit which controls the integrated output values of the first and second light-emitting sections based on the comparison result, and a light-emitting section selecting section which selects a light-emitting section supplied with an output signal of the integrated output value control circuit from the first and second light-emitting sections,
wherein the integrated output values contain light emission intensities and light emission periods of the first and second light-emitting sections, the light emission periods of the first and second light-emitting sections are synchronized with an exposure period of the image pickup element and at least one of the light emission intensities and light emission periods of the first and second light-emitting sections are independently controlled within the exposure period, and
wherein the integrated output value control section compares the light emission period with the exposure period of the image pickup element when it is detected in a comparison by a comparator that the reference level is larger than the dimming signal and controls at least one of the light emission intensities and light emission peri- ods of the first and second light-emitting sections based on the comparison result obtained at this time.

2. The light source device according to claim 1, wherein at least one light-emitting section of the first and second light-emitting sections is caused to emit light with light emission intensity higher than a rated level in a preset period of time.

3. The light source device according to claim 1, wherein the integrated output value control section compares the light emission intensities of the first and second light-emitting sections with a preset value larger than the rated level when it is detected in the comparison by the comparator that the reference level is smaller than the dimming signal and controls the light emission intensities or light emission periods of the first and second light-emitting sections based on the comparison result obtained at this time.

4. The light source device according to claim 1, wherein the first and second light-emitting sections are two LEDs associated with R, G, or B.

5. An image pickup device comprising:
a first light-emitting section which generates illumination light to be applied to a subject,
a second light-emitting section which generates illumination light with wavelength different from the illumination light generated from the first light- emitting section,
an image pickup element which photographs the subject,
a drive signal generating section which generates a drive signal to drive the image pickup element, and
an integrated output value control section which independently controls integrated output values of the first light-emitting section and second light-emitting section in synchronism with the drive signal generated from the drive signal generating section,
wherein the integrated output value control section includes a comparator which compares a dimming signal generated based on an image pickup signal from an image pickup element which photographs the subject with a reference level, an integrated output value control circuit which controls the integrated output values of the first and second light-emitting sections based on the comparison result, and a light-emitting section selecting section which selects a light-emitting section supplied with an output signal of the integrated output value control circuit from the first and second light-emitting sections,
wherein the integrated output values contain light emission intensities and light emission periods of the first and second light-emitting sections, the light emission periods of the first and second light-emitting sections are synchronized with an exposure period of the image pickup element and at least one of the light emission intensities and light emission periods of the first and second light-emitting sections are independently controlled within the exposure period, and
wherein the integrated output value control section compares the light emission period with the exposure period of the image pickup element when it is detected in the comparison by the comparator that the reference level is larger than the dimming signal and controls at least one of the light emission intensities and light emission periods of the first and second light-emitting sections based on the comparison result obtained at this time.

6. The image pickup device according to claim 5, wherein at least one light-emitting section of the first and second light-emitting sections is caused to emit light with light emission intensity higher than the rated level in a preset period of time.

7. The image pickup device according to claim 5, wherein the integrated output value control section compares the light emission intensities of the first and second light-emitting sections with a preset value larger than the rated level when it is detected in the comparison by the comparator that the reference level is smaller than the dimming signal and controls the light emission intensities or light emission periods of the first and second light-emitting sections based on the comparison result obtained at this time.

8. The image pickup device according to claim 5, wherein the first and second light-emitting sections are two LEDs associated with R, G, or B.

* * * * *